(12) United States Patent
Barnes et al.

(10) Patent No.: US 8,829,169 B2
(45) Date of Patent: Sep. 9, 2014

(54) **ASSAY FOR IMIDAZOLINONE RESISTANCE MUTATIONS IN *BRASSICA* SPECIES**

(75) Inventors: Stephen Barnes, Petit-Hallet (BE); Sigrid Vanstraelen, Nieuwerkerken (BE)

(73) Assignee: Monsanto Canada Inc., Winnipeg (CA)

( * ) Notice: Subject to any disclaimer, the term of this patent is extended or adjusted under 35 U.S.C. 154(b) by 6 days.

(21) Appl. No.: 12/545,147

(22) Filed: Aug. 21, 2009

(65) Prior Publication Data

US 2011/0034681 A1  Feb. 10, 2011

Related U.S. Application Data

(62) Division of application No. 10/695,546, filed on Oct. 28, 2003, now Pat. No. 7,595,177.

(60) Provisional application No. 60/421,994, filed on Oct. 29, 2002.

(51) Int. Cl.
*C07H 21/02* (2006.01)
*C07H 21/04* (2006.01)
*C12Q 1/68* (2006.01)
*C12P 19/34* (2006.01)

(52) U.S. Cl.
CPC ........ *C12Q 1/6895* (2013.01); *C12Q 2600/156* (2013.01)
USPC .... 536/23.1; 536/24.3; 536/24.31; 536/24.33

(58) Field of Classification Search
None
See application file for complete search history.

(56) References Cited

U.S. PATENT DOCUMENTS

| | | | |
|---|---|---|---|
| 6,100,030 A | 8/2000 | McCasky Feazel et al. | |
| 6,114,116 A | 9/2000 | Lemieux et al. | |
| 6,207,425 B1 | 3/2001 | Liu et al. | |
| 6,358,686 B1 | 3/2002 | Lemieux et al. | |
| 2002/0120962 A1 | 8/2002 | Charne et al. | |

FOREIGN PATENT DOCUMENTS

| | | |
|---|---|---|
| CA | 1 335 412 | 5/1995 |
| CA | 2 340 282 | 9/2001 |
| EP | 0502588 A2 | 3/1986 |
| EP | 0 284 419 B1 | 5/1994 |
| WO | WO 01/92512 A2 | 12/2001 |

OTHER PUBLICATIONS

Hung, G.C., "Species-specific amplification by PCR of ribosomal DNA from some equine strongyles," *Parasitology*, 1999, vol. 119 (Pt. 1), pp. 69-80.
Sathasivan, K., "Molecular Basis of Imidazolinone Herbicide Resistance in *Arabidopsis thaliana* var Columbia,"*Plant Physiol*, 1991, vol. 97(3),pp. 1044-1050.
Shi, X-B, et al., "Identification of p53 mutations in archival prostate tumors. Sensitivity of an optimized single-strand conformational polymorphism (SSCP) assay," *Diagn Mol Pathol*, 1996, vol. 5(4), pp. 271-278.
ORF Finder, National Center for Biotechnology Information BLAST printout (1998).
Rutledge, R., et al., *J. Mol. Gen. Genet.*, 1991, vol. 229, pp. 31-40.
Wagner, J. et al., "Identification of ALS inhibitor-resistant *Amaranthus* biotypes using polymerase chain reaction amplification of . . .", 2002, *Weed Research*, vol. 42, pp. 280-286.
Wiersma, et al., *Mol. Gen. Genet.*, 1989, vol. 219, pp. 413-420.
ClustalW Multiple Sequence Alignment Results, Baylor College of Medicine Search Launcer (1998).
*Germination: the magazine of the Canadian seed industry*, 2001, vol. 5(3), p. 14.
Hamajima, N. et al., *Qiagen News*, 2001, vol. 4, pp. 3-4.
Hattori, J. et al., *J. Mol. Gen. Genet.*, 1995, pp. 419-425.

*Primary Examiner* — Stephen Kapushoc
(74) *Attorney, Agent, or Firm* — Womble Carlyle Sandridge & Rice LLP

(57) ABSTRACT

The invention provides methods and oligonucleotide primers for assaying *Brassica napus* plants for the presence or absence of mutations that confer resistance to imidazolinone herbicides. Specifically, the methods and primers of the invention are useful for detecting the PM1 mutation of the *B. napus* AHAS1 gene and the PM2 mutation of the *B. napus* AHAS3 gene.

3 Claims, 13 Drawing Sheets

```
SEQ ID NO:1    GCTAAACCTTCTNNCAAATCCCCTCTACNNATTNNCAGATTCTNNCTTNCNTTCTNCTTA

SEQ ID NO:3              TTCTTCCAAATCCCCTCTACCCATTTCCAGATTCTCCCTTCCCTTCTCCTTA

#61                            .........  ......*.***** *.**..*********
SEQ ID NO:1    ACCCCACAGAAAGACTCCTCCCGTCTCCACCGTCCTCTCGCCATCTCCGNCGTTCTCAAC
SEQ ID NO:2                        GTCTCCACCGTCCTCTCGCCATCTNCGCCGTTCTCAAC
SEQ ID NO:3    ACCCCACAGAAAGACTCCTCCNGTCTCCACNGTCCTCTCGCCATNTCCGCNGTTCTCAAC
SEQ ID NO:4                                        TNGCCATNTCCGCCGTTCTCAAC

#121           ***** **.*****************.*******************************.**.
SEQ ID NO:1    TCACCCGTCAATGTCGCACCTCCTTCCCCTGAAAAAACCGACAAGAACAAGACTTTCGTC
SEQ ID NO:2    TCACCCGTCAATGTCGCACCTCCTTNCCCTGAAAAAACCGACAAGAACAAGACTTTCGTN
SEQ ID NO:3    TCACCNGTCAATGTCGCACCTCCTTCCCCTGAAAAAACCGACAAGAACAAGACTTTCGTC
SEQ ID NO:4    TCACCNGTNAATGTCGCACCTCCTTCCCCTGAAAAAACCGACAAGAACAAGACTTTNGTC

#181           *****.********.*********************************************
SEQ ID NO:1    TCCCGCTACGCTCCCGACGAGCCCCGCAAGGGTGCTGATATCCTCGTCGAAGCCCTCGAG
SEQ ID NO:2    TCCCGCTACGCTCCCGACGAGCCCCGCAAGGGTGCTGATATCCTCGTCGAAGCCCTCGAG
SEQ ID NO:3    TCCCGCTACGCTCCCGACGAGCCCCGCAAGGGTGCTGATATCCTCGTCGAAGCCCTCGAG
SEQ ID NO:4    TCCCGNTACGCTCCNGACGAGCCCCGCAAGGGTGCTGATATCCTCGTCGAAGCCCTCGAG

#241           ************************************************************
SEQ ID NO:1    CGTCAAGGCGTCGAAACCGTCTTTGCTTATCCCGGAGGTGCTTCCATGGAGATCCACCAA
SEQ ID NO:2    CGTCAAGGCGTCGAAACCGTCTTTGCTTATCCCGGAGGTGCTTCCATGGAGATCCACCAA
SEQ ID NO:3    CGTCAAGGCGTCGAAACCGTCTTTGCTTATCCCGGAGGTGCTTCCATGGAGATCCACCAA
SEQ ID NO:4    CGTCAAGGCGTCGAAACCGTCTTTGCTTATCCCGGAGGTGCTTCCATGGAGATCCACCAA

#301           ************************************************************
SEQ ID NO:1    GCCTTGACTCGCTCCTCCACCATCCGTAACGTCCTTCCCCGTCACGAACAAGGAGGAGTC
SEQ ID NO:2    GCCTTGACTCGCTCCTCCACCATCCGTAACGTCCTTCCCCGTCACGAACAAGGAGGAGTC
SEQ ID NO:3    GCCTTGACTCGCTCCTCCACCATCCGTAACGTCCTTCCCCGTCACGAACAAGGAGGAGTC
SEQ ID NO:4    GCCTTGACTCGCTCCTCCACCATCCGTAACGTCCTTCCCCGTCACGAACAAGGAGGAGTC

#361           ************************************************************
SEQ ID NO:1    TTCGCCGCCGAGGGTTACGCTCGTTCCTCCGGCAAACCGGGAATCTGCATAGCCACTTCG
SEQ ID NO:2    TTCGCCGCCGAGGGTTACGCTCGTTCCTCCGGCAAACCGGGAATCTGCATAGCCACTTCG
SEQ ID NO:3    TTCGCCGCCGAGGGTTACGCTCGTTCCTCCGGCAAACCGGGAATCTGCATAGCCACTTCG
SEQ ID NO:4    TTCGCCGCCGAGGGGTTACGCTCGTTCCTCCGGCAAACCGGGAATCTGCATAGCCACTTCG

#421           ************************************************************
SEQ ID NO:1    GGTCCCGGAGCTACCAACCTCGTCAGCGGGTTAGCAGACGCGATGCTTGACAGTGTTCCT
SEQ ID NO:2    GGTCCCGGAGCTACCAACCTCGTCAGCGGGTTAGCAGACGCGATGCTTGACAGTGTTCCT
SEQ ID NO:3    GGTCCCGGAGCTACCAACCTCGTCAGCGGGTTAGCAGACGCGATGCTTGACAGTGTTCCT
SEQ ID NO:4    GGTCCCGGAGCTACCAACCTCGTCAGCGGGTTAGCAGACGCGATGCTTGACAGTGTTCCT

#481           ************************************************************
SEQ ID NO:1    CTTGTCGCCATTACAGGACAGGTCCCTCGCCGGATGATCGGTACTGACGCCTTCCAAGAG
SEQ ID NO:2    CTTGTCGCCATTACAGGACAGGTCCCTCGCCGGATGATCGGTACTGACGCCTTCCAAGAG
SEQ ID NO:3    CTTGTCGCCATTACAGGACAGGTCCCTCGCCGGATGATCGGTACTGACGCCTTCCAAGAG
SEQ ID NO:4    CTTGTCGCCATTACAGGACAGGTCCCTCGCCGGATGATCGGTACTGACGCCTTCCAAGAG

#541           ************************************************************
SEQ ID NO:1    ACACCAATCGTTGAGGTAACGAGGTCTATTACGAAACATAACTATTTGGTGATGGATGTT
SEQ ID NO:2    ACACCAATCGTTGAGGTAACGAGGTCTATTACGAAACATAACTATTTGGTGATGGATGTT
SEQ ID NO:3    ACACCAATCGTTGAGGTAACGAGGTCTATTACGAAACATAACTATTTGGTGATGGATGTT
SEQ ID NO:4    ACACCAATCGTTGAGGTAACGAGGTCTATTACGAAACATAACTATTTGGTGATGGATGTT

#601           ********************************************************.***
SEQ ID NO:1    GATGACATACCTAGGATCGTTCAAGAAGCTTTCTTTCTAGCTACTTCCGGTAGACCNGGA
SEQ ID NO:2    GATGACATACCTAGGATCGTTCAAGAAGCTTTCTTTCTAGCTACTTCCGGTAGACCCGGA
SEQ ID NO:3    GATGACATACCTAGGATCGTTCAAGAAGCTTTCTTTCTAGCTACTTCCGGTAGACCCGGA
SEQ ID NO:4    GATGACATACCTAGGATCGTTCAAGAAGCTTTCTTTCTAGCTACTTCCGGTAGACCCGGA

#661           ************************************************************
SEQ ID NO:1    CCGGTTTTGGTTGATGTTCCTAAGGATATTCAGCAGCAGCTTGCGATTCCTAACTGGGAT
SEQ ID NO:2    CCGGTTTTGGTTGATGTTCCTAAGGATATTCAGCAGCAGCTTGCGATTCCTAACTGGGAT
SEQ ID NO:3    CCGGTTTTGGTTGATGTTCCTAAGGATATTCAGCAGCAGCTTGCGATTCCTAACTGGGAT
SEQ ID NO:4    CCGGTTTTGGTTGATGTTCCTAAGGATATTCAGCAGCAGCTTGCGATTCCTAACTGGGAT
```

Figure 1A

```
#721          ******************************  **********************************
SEQ ID NO:1   CAACCTATGCGCTTACCTGGCTACATGTNTAGGTTGCCTCAGCCTCCGGAAGTTTCTCAG
SEQ ID NO:2   CAACCTATGCGCTTACCTGGCTACATGTCTAGGTTGCCTCAGCCTCCGGAAGTTTCTCAG
SEQ ID NO:3   CAACCTATGCGCTTACCTGGCTACATGTCTAGGTTGCCTCAGCCTCCGGAAGTTTCTCAG
SEQ ID NO:4   CAACCTATGCGCTTACCTGGCTACATGTNTAGGTTGCCTCAGCCTCCGGAAGTTTCTCAG

#781          ************************************************************
SEQ ID NO:1   TTAGGTCAGATCGTTAGGTTGATCTCGGAGTCTAAGAGGCCTGTTTTGTACGTTGGTGGT
SEQ ID NO:2   TTAGGTCAGATCGTTAGGTTGATCTCGGAGTCTAAGAGGCCTGTTTTGTACGTTGGTGGT
SEQ ID NO:3   TTAGGTCAGATCGTTAGGTTGATCTCGGAGTCTAAGAGGCCTGTTTTGTACGTTGGTGGT
SEQ ID NO:4   TTAGGTCAGATCGTTAGGTTGATCTCGGAGTCTAAGAGGCCTGTTTTGTACGTTGGTGGT

#841          ************************************************************
SEQ ID NO:1   GGAAGCTTGAACTCGAGTGAAGAACTGGGGAGATTTGTCGAGCTTACTGGGATCCCCGTT
SEQ ID NO:2   GGAAGCTTGAACTCGAGTGAAGAACTGGGGAGATTTGTCGAGCTTACTGGGATCCCCGTT
SEQ ID NO:3   GGAAGCTTGAACTCGAGTGAAGAACTGGGGAGATTTGTCGAGCTTACTGGGATCCCCGTT
SEQ ID NO:4   GGAAGCTTGAACTCGAGTGAAGAACTGGGGAGATTTGTCGAGCTTACTGGGATCCCCGTT

#901          ************************************************************
SEQ ID NO:1   GCGAGTACTTTGATGGGGCTTGGCTCTTATCCTTGTAACGATGAGTTGTCCCTGCAGATG
SEQ ID NO:2   GCGAGTACTTTGATGGGGCTTGGCTCTTATCCTTGTAACGATGAGTTGTCCCTGCAGATG
SEQ ID NO:3   GCGAGTACTTTGATGGGGCTTGGCTCTTATCCTTGTAACGATGAGTTGTCCCTGCAGATG
SEQ ID NO:4   GCGAGTACTTTGATGGGGCTTGGCTCTTATCCTTGTAACGATGAGTTGTCCCTGCAGATG

#961          ************************************************************
SEQ ID NO:1   CTTGGCATGCACGGGACTGTGTATGCTAACTACGCTGTGGAGCATAGTGATTTGTTGCTG
SEQ ID NO:2   CTTGGCATGCACGGGACTGTGTATGCTAACTACGCTGTGGAGCATAGTGATTTGTTGCTG
SEQ ID NO:3   CTTGGCATGCACGGGACTGTGTATGCTAACTACGCTGTGGAGCATAGTGATTTGTTGCTG
SEQ ID NO:4   CTTGGCATGCACGGGACTGTGTATGCTAACTACGCTGTGGAGCATAGTGATTTGTTGCTG

#1021         ******************************.*****************************
SEQ ID NO:1   GCGTTTGGTGTTAGGTTTGATGACCGTGTCACGGGAAAGCTCGAGGCTTTCGCTAGCAGG
SEQ ID NO:2   GCGTTTGGTGTTAGGTTTGATGACCGTGTCACGGGAAAGCTCGAGGCTTTCGCTAGCAGG
SEQ ID NO:3   GCGTTTGGTGTTAGGTTTGATGNCCGTGTCACGGGAAAGCTCGAGGCTTTCGCTAGCAGG
SEQ ID NO:4   GCGTTTGGTGTTAGGTTTGATGACCGTGTCACGGGAAAGCTCGAGGCTTTCGCTAGCAGG

#1081         ************************************************************
SEQ ID NO:1   GCTAAAATTGTGCACATAGACATTGATTCTGCTGAGATTGGGAAGAATAAGACACCTCAC
SEQ ID NO:2   GCTAAAATTGTGCACATAGACATTGATTCTGCTGAGATTGGGAAGAATAAGACACCTCAC
SEQ ID NO:3   GCTAAAATTGTGCACATAGACATTGATTCTGCTGAGATTGGGAAGAATAAGACACCTCAC
SEQ ID NO:4   GCTAAAATTGTGCACATAGACATTGATTCTGCTGAGATTGGGAAGAATAAGACACCTCAC

#1141         ************************************************************
SEQ ID NO:1   GTGTCTGTGTGTGGTGATGTAAAGCTGGCTTTGCAAGGGATGAACAAGGTTCTTGAGAAC
SEQ ID NO:2   GTGTCTGTGTGTGGTGATGTAAAGCTGGCTTTGCAAGGGATGAACAAGGTTCTTGAGAAC
SEQ ID NO:3   GTGTCTGTGTGTGGTGATGTAAAGCTGGCTTTGCAAGGGATGAACAAGGTTCTTGAGAAC
SEQ ID NO:4   GTGTCTGTGTGTGGTGATGTAAAGCTGGCTTTGCAAGGGATGAACAAGGTTCTTGAGAAC

#1201         ************************************************************
SEQ ID NO:1   CGGGCGGAGGAGCTCAAGCTTGATTTCGGTGTTTGGAGGAGTGAGTTGAGCGAGCAGAAA
SEQ ID NO:2   CGGGCGGAGGAGCTCAAGCTTGATTTCGGTGTTTGGAGGAGTGAGTTGAGCGAGCAGAAA
SEQ ID NO:3   CGGGCGGAGGAGCTCAAGCTTGATTTCGGTGTTTGGAGGAGTGAGTTGAGCGAGCAGAAA
SEQ ID NO:4   CGGGCGGAGGAGCTCAAGCTTGATTTCGGTGTTTGGAGGAGTGAGTTGAGCGAGCAGAAA

#1261         ************************************************************
SEQ ID NO:1   CAGAAGTTCCCTTTGAGCTTCAAAACGTTTGGAGAAGCCATTCCTCCGCAGTACGCGATT
SEQ ID NO:2   CAGAAGTTCCCTTTGAGCTTCAAAACGTTTGGAGAAGCCATTCCTCCGCAGTACGCGATT
SEQ ID NO:3   CAGAAGTTCCCTTTGAGCTTCAAAACGTTTGGAGAAGCCATTCCTCCGCAGTACGCGATT
SEQ ID NO:4   CAGAAGTTCCCTTTGAGCTTCAAAACGTTTGGAGAAGCCATTCCTCCGCAGTACGCGATT

#1321         ************************************************************
SEQ ID NO:1   CAGATCCTCGACGAGCTAACCGAAGGGAAGGCAATTATCAGTACTGGTGTTGGACAGCAT
SEQ ID NO:2   CAGATCCTCGACGAGCTAACCGAAGGGAAGGCAATTATCAGTACTGGTGTTGGACAGCAT
SEQ ID NO:3   CAGATCCTCGACGAGCTAACCGAAGGGAAGGCAATTATCAGTACTGGTGTTGGACAGCAT
SEQ ID NO:4   CAGATCCTCGACGAGCTAACCGAAGGGAAGGCAATTATCAGTACTGGTGTTGGACAGCAT
```

Figure 1B

```
#1381           ****************************************************
SEQ ID NO:1     CAGATGTGGGCGGCGCAGTTTTACAAGTACAGGAAGCCGAGACAGTGGCTGTCGTCATCA
SEQ ID NO:2     CAGATGTGGGCGGCGCAGTTTTACAAGTACAGGAAGCCGAGACAGTGGCTGTCGTCATCA
SEQ ID NO:3     CAGATGTGGGCGGCGCAGTTTTACAAGTACAGGAAGCCGAGACAGTGGCTGTCGTCATCA
SEQ ID NO:4     CAGATGTGGGCGGCGCAGTTTTACAAGTACAGGAAGCCGAGACAGTGGCTGTCGTCATCA

#1441           ******.*****************************************************
SEQ ID NO:1     GGCCTCGGAGCTATGGGTTTTGGACTTCCTGCTGCGATTGGAGCGTCTGTGGCGAACCCT
SEQ ID NO:2     GGCCTCGGAGCTATGGGTTTTGGACTTCCTGCTGCGATTGGAGCGTCTGTGGCGAACCCT
SEQ ID NO:3     GGCCTCGGAGCTATGGGTTTTGGACTTCCTGCTGCGATTGGAGCGTCTGTGGCGAACCCT
SEQ ID NO:4     GGCCTCNGAGCTATGGGTTTTGGACTTCCTGCTGCGATTGGAGCGTCTGTGGCGAACCCT

#1501           ************************************************************
SEQ ID NO:1     GATGCGATTGTTGTGGATATTGACGGTGATGGAAGCTTCATAATGAACGTTCAAGAGCTG
SEQ ID NO:2     GATGCGATTGTTGTGGATATTGACGGTGATGGAAGCTTCATAATGAACGTTCAAGAGCTG
SEQ ID NO:3     GATGCGATTGTTGTGGATATTGACGGTGATGGAAGCTTCATAATGAACGTTCAAGAGCTG
SEQ ID NO:4     GATGCGATTGTTGTGGATATTGACGGTGATGGAAGCTTCATAATGAACGTTCAAGAGCTG

#1561           ************************************************************
SEQ ID NO:1     GCCACAATCCGTGTAGAGAATCTTCCTGTGAAGATACTCTTGTTAAACAACCAGCATCTT
SEQ ID NO:2     GCCACAATCCGTGTAGAGAATCTTCCTGTGAAGATACTCTTGTTAAACAACCAGCATCTT
SEQ ID NO:3     GCCACAATCCGTGTAGAGAATCTTCCTGTGAAGATACTCTTGTTAAACAACCAGCATCTT
SEQ ID NO:4     GCCACAATCCGTGTAGAGAATCTTCCTGTGAAGATACTCTTGTTAAACAACCAGCATCTT

#1621           ************************************************************
SEQ ID NO:1     GGGATGGTCATGCAATGGGAAGATCGGTTCTACAAAGCTAACAGAGCTCACACTTATCTC
SEQ ID NO:2     GGGATGGTCATGCAATGGGAAGATCGGTTCTACAAAGCTAACAGAGCTCACACTTATCTC
SEQ ID NO:3     GGGATGGTCATGCAATGGGAAGATCGGTTCTACAAAGCTAACAGAGCTCACACTTATCTC
SEQ ID NO:4     GGGATGGTCATGCAATGGGAAGATCGGTTCTACAAAGCTAACAGAGCTCACACTTATCTC

#1681           ****************************.*******************************
SEQ ID NO:1     GGGGACCCGGCAAGGGAGAACGAGATCTTCCCTAACATGCTGCAGTTTGCAGGAGCTTGC
SEQ ID NO:2     GGGGACCCGGCAAGGGAGAACGAGATCTTNCCTAACATGCTGCAGTTTGCAGGAGCTTGC
SEQ ID NO:3     GGGGACCCGGCAAGGGAGAACGAGATCTTCCCTAACATGCTGCAGTTTGCAGGAGCTTGC
SEQ ID NO:4     GGGGACCCGGCAAGGGAGAACGAGATCTTCCCTAACATGCTGCAGTTTGCAGGAGCTTGC

#1741           ******************************.*****************************
SEQ ID NO:1     GGGATTCCAGCTGCGAGAGTGACGAAGAAAGAAGAACTCCGAGAAGCTATTCAGACAATG
SEQ ID NO:2     GGGATTCCAGCTGCGAGAGTGACGAAGAAAGAAGAACTCNGAGAAGCTATTCAGACAATG
SEQ ID NO:3     GGGATTCCAGCTGCGAGAGTGACGAAGAAAGAAGAACTCCGAGAAGCTATTCAGACAATG
SEQ ID NO:4     GGGATTCCAGCTGCGAGAGTGACGAAGAAAGAAGAACTCCGAGAAGCTATTCAGACAATG
```

PM1 Forward primer
                          SEQ ID NO:11
                        CATACCTGTTGGATGTGATAT
                        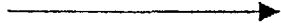

```
#1801           .***********.***********************************************
SEQ ID NO:1     CTGGATACACCAGGACCCATACCTGTTGGATGTGATATGTCCGCACCAAGAACATGTGTTA
SEQ ID NO:2     NTGGATACACCAGGNCCATACCTGTTGGATGTGATATGTCCGCACCAAGAACATGTGTTA
SEQ ID NO:3     CTGGATACACCAGGACCCATACCTGTTGGATGTGATATGTCCGCACCAAGAACATGTGTTA
SEQ ID NO:4     CTGGATACACCAGGACCCATACCTGTTGGATGTGATATGTCCGCACCAAGAACATGTGTTA
```

PM1

```
#1861           ************.***********************************************
SEQ ID NO:1     CCGATGATCCCAAATGGTGGCACTTTCAAAGATGTAATAACAGAAGGGGATGGTCGCACT
SEQ ID NO:2     CCGATGATCCCAAGTGGTGGCACTTTCAAAGATGTAATAACAGAAGGGGATGGTCGCACT
SEQ ID NO:3     CCGATGATCCCAAATGGTGGCACTTTCAAAGATGTAATAACAGAAGGGGATGGTCGCACT
SEQ ID NO:4     CCGATGATCCCAAGTGGTGGCACTTTCAAAGATGTAATAACAGAAGGGGATGGTCGCACT
```

Figure 1C

```
#1921                 ************************************************************
SEQ ID NO:1    AAGTACTGAGAGATGAAGCTGGTGATCGATCATATGGTAAAAGACTTAGTTTCAGTTTCC
SEQ ID NO:2    AAGTACTGAGAGATGAAGCTGGTGATCGATCATATGGTAAAAGACTTAGTTTCAGTTTCC
SEQ ID NO:3    AAGTACTGAGAGATGAAGCTGGTGATCGATCATATGGTAAAAGACTTAGTTTCAGTTTCC
SEQ ID NO:4    AAGTACTGAGAGATGAAGCTGGTGATCGATCATATGGTAAAAGACTTAGTTTCAGTTTCC

#1981                 ************************************************************
SEQ ID NO:1    AGTTTCTTTTGTGTGGTAATTTGGGTTTGTCAGTTGTTGTACTACTTTTGGTTGTTCCCA
SEQ ID NO:2    AGTTTCTTTTGTGTGGTAATTTGGGTTTGTCAGTTGTTGTACTACTTTTGGTTGTTCCCA
SEQ ID NO:3    AGTTTCTTTTGTGTGGTAATTTGGGTTTGTCAGTTGTTGTACTACTTTTGGTTGTTCCCA
SEQ ID NO:4    AGTTTCTTTTGTGTGGTAATTTGGGTTTGTCAGTTGTTGTACTACTTTTGGTTGTTCCCA

PM1 Reverse primer
                              SEQ ID NO:12
                          TGCATGAGCGACAACAACAAA
                          ◄─────────────────────
#2041                 **********.*******************************
SEQ ID NO:1    GACGTACTCGCTGTTGTTGTTTTGTTTCCTTTTTCTTTTATATATAA
SEQ ID NO:2    GACGTACTCGNTGTTGTTTTTGTTTCCTTTTTCTTTTATATAT
SEQ ID NO:3    GACGTACTCGCTGTTGTTGTTTTGTTTCCTTTTTCTTTTATATAT
SEQ ID NO:4    GACGTACTCGCTGTTGTTGTTTTGTTTCCTTTTTCTTTTATATATAA
```

SEQ ID NO:6        TCATTCATCATCTCTCTCTCATTTCTCTCTCTCTCTCATCTAACCATGGCGGCGGCAACA

61

SEQ ID NO:6        TCGTCTTCTCCGATCTCCTTAACCGCTAAACCTTCTTCCAAATCCCCTCTACCCATTTCC

121
SEQ ID NO:5                                                 ........ .....
SEQ ID NO:6        AGATTCTCCCTTCCCTTCTCCTTAACCCCACAGAAACCCTCCTCCCGTCTCCACCGTCCA
SEQ ID NO:7                TTCTCCTTAACCCCACAGAAACCCTCCTCCNGTCTCCACCGTCCA
SEQ ID NO:8                                                       GTCTCCACNGTCCA

181
SEQ ID NO:5        ......... .. ...................****************************
SEQ ID NO:6        CTCGCCATCTCCGCCGTTCTCAACTCACCCGTCAATGTCGCACCTGAAAAAACCGACAAG
SEQ ID NO:7        CTCGCCATCTCCGCCGTTCTCAACTCACCCGTCAATGTCGCACCTGAAAAAACCGACAAG
SEQ ID NO:8        CTCGCCATNTCCGCCGTTCTCAACTCACCCGTCAATGTCGCACCTGAAAAAACCGACAAG
                                                GTCAATGTCGCACCTGAAAAAACCGACAAG

241
SEQ ID NO:5        ******************* *************************** ****
SEQ ID NO:6        ATCAAGACTTTCATCTCCCGCTACGCTCCCGACGAGCCCCGCAAGGGTGCTGATATCCTC
SEQ ID NO:7        ATCAAGACTTTCATCTCCCGCTACGCTCCCGACGAGCCCCGCAAGGGTGCTGATATCCTC
SEQ ID NO:8        ATCAAGACTTTCATCTCCCGNTACGCTCCCGACGAGCCCCGCAAGGGTGCTGATATCCTC
                   ATCAAGACTTTCATCTCCCGNTACGCTCCCGACGAGCCCCGCAAGGGTGCTGATATCCTC

301
SEQ ID NO:5        **********************************************************.*
SEQ ID NO:6        GTGGAAGCCCTCGAGCGTCAAGGCGTCGAAACCGTCTTCGCTTATCCCGGAGGTGCCTCC
SEQ ID NO:7        GTGGAAGCCCTCGAGCGTCAAGGCGTCGAAACCGTCTTCGCTTATCCCGGAGGTGCCTCC
SEQ ID NO:8        GTGGAAGCCCTCGAGCGTCAAGGCGTCGAAACCGTCTTCGCTTATCCCGGAGGTGCCTCC
                   GTGGAAGCCCTCGAGCGTCAAGGCGTCGAAACCGTCTTCGCTTATCCCGGAGGTGCCTCC

361
SEQ ID NO:5        ************************************************************
SEQ ID NO:6        ATGGAGATCCACCAAGCCTTGACTCGCTCCTCCACCATCCGTAACGTCCTCCCCCGTCAC
SEQ ID NO:7        ATGGAGATCCACCAAGCCTTGACTCGCTCCTCCACCATCCGTAACGTCCTCCCCCGTCAC
SEQ ID NO:8        ATGGAGATCCACCAAGCCTTGACTCGCTCCTCCACCATCCGTAACGTCCTCCCCCGTCAC
                   ATGGAGATCCACCAAGCCTTGACTCGCTCCTCCACCATCCGTAACGTCCTCCCCCGTCAC

421
SEQ ID NO:5        ************************************************************
SEQ ID NO:6        GAACAAGGAGGAGTCTTCGCCGCCGAGGGTTACGCTCGTTCCTCCGGCAAACCGGGAATC
SEQ ID NO:7        GAACAAGGAGGAGTCTTCGCCGCCGAGGGTTACGCTCGTTCCTCCGGCAAACCGGGAATC
SEQ ID NO:8        GAACAAGGAGGAGTCTTCGCCGCCGAGGGTTACGCTCGTTCCTCCGGCAAACCGGGAATC
                   GAACAAGGAGGAGTCTTCGCCGCCGAGGGTTACGCTCGTTCCTCCGGCAAACCGGGAATC

481
SEQ ID NO:5        ************************************************************
SEQ ID NO:6        TGCATAGCCACTTCGGGTCCCGGAGCTACCAACCTCGTCAGCGGGTTAGCCGACGCGATG
SEQ ID NO:7        TGCATAGCCACTTCGGGTCCCGGAGCTACCAACCTCGTCAGCGGGTTAGCCGACGCGATG
SEQ ID NO:8        TGCATAGCCACTTCGGGTCCCGGAGCTACCAACCTCGTCAGCGGGTTAGCCGACGCGATG
                   TGCATAGCCACTTCGGGTCCCGGAGCTACCAACCTCGTCAGCGGGTTAGCCGACGCGATG

541
SEQ ID NO:5        ************************************************************
SEQ ID NO:6        CTTGACAGTGTTCCTCTCGTCGCCATCACAGGACAGGTCCCTCGCCGGATGATCGGTACT
SEQ ID NO:7        CTTGACAGTGTTCCTCTCGTCGCCATCACAGGACAGGTCCCTCGCCGGATGATCGGTACT
SEQ ID NO:8        CTTGACAGTGTTCCTCTCGTCGCCATCACAGGACAGGTCCCTCGCCGGATGATCGGTACT
                   CTTGACAGTGTTCCTCTCGTCGCCATCACAGGACAGGTCCCTCGCCGGATGATCGGTACT

Figure 2A

```
#601
SEQ ID NO:5   GACGCGTTCCAAGAGACGCCAATCGTTGAGGTAACGAGGTCTATTACGAAACATAACTAT
SEQ ID NO:6   GACGCGTTCCAAGAGACGCCAATCGTTGAGGTAACGAGGTCTATTACGAAACATAACTAT
SEQ ID NO:7   GACGCGTTCCAAGAGACGCCAATCGTTGAGGTAACGAGGTCTATTACGAAACATAACTAT
SEQ ID NO:8   GACGCGTTCCAAGAGACGCCAATCGTTGAGGTAACGAGGTCTATTACGAAACATAACTAT

#661
SEQ ID NO:5   CTGGTGATGGATGTTGATGACATACCTAGGATCGTTCAAGAAGCATTCTTTCTAGCTACT
SEQ ID NO:6   CTGGTGATGGATGTTGATGACATACCTAGGATCGTTCAAGAAGCATTCTTTCTAGCTACT
SEQ ID NO:7   CTGGTGATGGATGTTGATGACATACCTAGGATCGTTCAAGAAGCATTCTTTCTAGCTACT
SEQ ID NO:8   CTGGTGATGGATGTTGATGACATACCTAGGATCGTTCAAGAAGCTTTCTTTCTAGCTACT

#721
SEQ ID NO:5   TCCGGTAGACCCGGACCGGTTTTGGTTGATGTTCCTAAGGATATTCAGCAGCAGCTTGCG
SEQ ID NO:6   TCCGGTAGACCCGGACCGGTTTTGGTTGATGTTCCTAAGGATATTCAGCAGCAGCTTGCG
SEQ ID NO:7   TCCGGTAGACCCGGACCGGTTTTGGTTGATGTTCCTAAGGATATTCAGCAGCAGCTTGCG
SEQ ID NO:8   TCCGGTAGACCCGGACCGGTTTTGGTTGATGTTCCTAAGGATATTCAGCAGCAGCTTGCG

#781
SEQ ID NO:5   ATTCCTAACTGGGATCAACCTATGCGCTTGCCTGGCTACATGTCTAGGCTGCCTCAGCCA
SEQ ID NO:6   ATTCCTAACTGGGATCAACCTATGCGCTTGCCTGGCTACATGTCTAGGCTGCCTCAGCCA
SEQ ID NO:7   ATTCCTAACTGGGATCAACCTATGCGCTTGCCTGGCTACATGTCTAGGCTGCCTCAGCCA
SEQ ID NO:8   ATTCCTAACTGGGATCAACCTATGCGCTTGCCTGGCTACATGTCTAGGCTGCCTCAGCCA

#841
SEQ ID NO:5   CCGNAAGTTTCTCAGTTAGGCCAGATCGTTAGGTTGATCTCGGAGTCTAAGAGGCCTGTT
SEQ ID NO:6   CCGGAAGTTTCTCAGTTAGGCCAGATCGTTAGGTTGATCTCGGAGTCTAAGAGGCCTGTT
SEQ ID NO:7   CCGNAAGTTTCTCAGTTAGGCCAGATCGTTAGGTTGATCTCGGAGTCTAAGAGGCCTGTT
SEQ ID NO:8   CCGNAAGTTTCTCAGTTAGGTCAGATCGTTAGGTTGATCTCGGAGTCTAAGAGGCCTGTT

#901
SEQ ID NO:5   TTGTACGTTGGTGGTGGAAGCTTGAACTCGAGTGAAGAACTGGGGAGATTTGTCGAGCTT
SEQ ID NO:6   TTGTACGTTGGTGGTGGAAGCTTGAACTCGAGTGAAGAACTGGGGAGATTTGTCGAGCTT
SEQ ID NO:7   TTGTACGTTGGTGGTGGAAGCTTGAACTCGAGTGAAGAACTGGGGAGATTTGTCGAGCTT
SEQ ID NO:8   TTGTACGTTGGTGGTGGAAGCTTGAACTCGAGTGAAGAACTGGGGAGATTTGTCGAGCTT

#961
SEQ ID NO:5   ACTGGGATCCCTGTTGCGAGTACGTTGATGGGGCTTGGCTCTTATCCTTGTAACGATGAG
SEQ ID NO:6   ACTGGGATCCCTGTTGCGAGTACGTTGATGGGGCTTGGCTCTTATCCTTGTAACGATGAG
SEQ ID NO:7   ACTGGGATCCCTGTTGCGAGTACGTTGATGGGGCTTGGCTCTTATCCTTGTAACGATGAG
SEQ ID NO:8   ACTGGGATCCCTGTTGCGAGTACGTTGATGGGGCTTGGCTCTTATCCTTGTAACGATGAG

#1021
SEQ ID NO:5   TTGTCCCTGCAGATGCTTGGCATGCACGGGACTGTGTATGCTAACTACGCTGTGGAGCAT
SEQ ID NO:6   TTGTCCCTGCAGATGCTTGGCATGCACGGGACTGTGTATGCTAACTACGCTGTGGAGCAT
SEQ ID NO:7   TTGTCCCTGCAGATGCTTGGCATGCACGGGACTGTGTATGCTAACTACGCTGTGGAGCAT
SEQ ID NO:8   TTGTCCCTGCAGATGCTTGGCATGCACGGGACTGTGTATGCTAACTACGCTGTGGAGCAT

#1081
SEQ ID NO:5   AGTGATTTGTTGCTGGCGTTTGGTGTTAGGTTTNATGACCGTGTNNNNNNNNNNNNNNNN
SEQ ID NO:6   AGTGATTTGTTGCTGGCGTTTGGTGTTAGGTTTGATGACCGTGTCACGGGAAAGCTCGAG
SEQ ID NO:7   AGTGATTTGTTGCTGGCGTTTGGTGTTAGGTTTGATGACCGTGTCACGGGAAAGCTCGAG
SEQ ID NO:8   AGTGATTTGTTGCTGGCGTTTGGTGTTAGGTTTGATGACCGTGTCACGGGAAAGCTCGAG

#1141
SEQ ID NO:5   NNNNNNNNNNNNNNNNNNNNNNNNNNNNNNNNNNNNNNNNNNNNNNNNNNNNNNNNNNNN
SEQ ID NO:6   GCGTTTGCGAGCAGGGCTAAGATTGTGCACATAGACATTGATTCTGCTGAGATTGGGAAG
SEQ ID NO:7   GCGTTTGCGAGCAGGGCTAAGATTGTGCACATAGACATTGATTCTGCTGAGATTGGGAAG
SEQ ID NO:8   GCGTTTGCGAGCAGGGCTAAGATTGTGCACATAGACATTGATTCTGCTGAGATTGGGAAG

#1201
SEQ ID NO:5   NNNNNNNNNNNNNNNNNNNNNNNNNNNNNNNNNNNNNNNNNNNNNNNNNNNNNNNNNNNN
SEQ ID NO:6   AATAAGACACCTCACGTGTCTGTGTGTGGTGATGTAAAGCTGGCTTTGCAAGGGATGAAC
SEQ ID NO:7   AATAAGACACCTCACGTGTCTGTGTGTGGTGATGTAAAGCTGGCTTTGCAAGGGATGAAC
SEQ ID NO:8   AATAANACACCTCACGTGTCTGTGTGTGGTGATGTAAAGCTGGCTTTGCAAGGGATGAAC
```

Figure 2B

```
#1261
SEQ ID NO:5   NNNNNNNNNNNNNNNNNNNNNNNNNNNNNNNNNNNNNNNNNNNNNNNNNNNNNNNNNNNN
SEQ ID NO:6   AAGGTTCTTGAGAACCGGGCGGAGGAGCTCAAGCTTGATTTCGGTGTTTGGAGGAGTGAG
SEQ ID NO:7   AAGGTTCTTGAGAACCGGGCGGAGGAGCTCAAGCTTGATTTCGGTGTTTGGAGGAGTGAG
SEQ ID NO:8   AAGGTTCTTGAGAACCGGGCGGAGGAGCTCAAGCTTGATTTCGGTGTTTGGAGGAGTGAG

#1321
SEQ ID NO:5   NNNNNNNNNNNNNNNNNNNNNNNNNNNNNNNNNNNNNNNNNNNNNNNNNNNNNNNNNNNN
SEQ ID NO:6   TTGAGCGAGCAGAAACAGAAGTTCCCGTTGAGCTTCAAAACGTTTGGAGAAGCCATTCCT
SEQ ID NO:7   TTGAGCGAGCAGAAACAGAAGTTCCCGTTGAGCTTCAAAACGTTTGGAGAAGCCATTCCT
SEQ ID NO:8   TTGAGCGAGCAGAAACAGAAGTTCCCGTTGAGCTTCAAAACGTTTGGAGAAGCCATTCCT

#1381                              ****************************
SEQ ID NO:5   NNNNNNNNNNNNNNNNNNNNNNNNNNNNNNNAGCTAACCCAAGGGAAGGCAATTATCAGTACT
SEQ ID NO:6   CCGCAGTACGCGATTCAGGTCCTAGACGAGCTAACCCAAGGGAAGGCAATTATCAGTACT
SEQ ID NO:7   CCGCAGTACGCGATTCAGGTCCTAGACGAGCTAACCCAAGGGAAGGCAATTATCAGTACT
SEQ ID NO:8   CCGCAGTACGCGATTCAGGTCCTAGACGAGCTAACCCAAGGGAAGGCAATTATCAGTACT

#1441         ************************************************************
SEQ ID NO:5   GGTGTTGGACAGCATCAGATGTGGGCGGCGCAGTTTTACAAGTACAGGAAGCCGAGGCAG
SEQ ID NO:6   GGTGTTGGACAGCATCAGATGTGGGCGGCGCAGTTTTACAAGTACAGGAAGCCGAGGCAG
SEQ ID NO:7   GGTGTTGGACAGCATCAGATGTGGGCGGCGCAGTTTTACAAGTACAGGAAGCCGAGGCAG
SEQ ID NO:8   GGTGTTGGACAGCATCAGATGTGGGCGGCGCAGTTTTACAAGTACAGGAAGCCGAGGCAG

PM2 Region Forward primer
                             SEQ ID NO:15
                          ACTCGGAGCTATGGGTTTC
                          ─────────────────▶
#1501         ************************************************************
SEQ ID NO:5   TGGCTGTCGTCCTCAGGACTCGGAGCTATGGGTTTCGGACTTCCTGCTGCGATTGGAGCG
SEQ ID NO:6   TGGCTGTCGTCCTCAGGACTCGGAGCTATGGGTTTCGGACTTCCTGCTGCGATTGGAGCG
SEQ ID NO:7   TGGCTGTCGTCCTCAGGACTCGGAGCTATGGGTTTCGGACTTCCTGCTGCGATTGGAGCG
SEQ ID NO:8   TGGCTGTCGTCCTCAGGACTCGGAGCTATGGGTTTCGGACTTCCTGCTGCGATTGGAGCG

#1561         ************************************************************
SEQ ID NO:5   TCTGTGGCGAACCCTGATGCGATTGTTGTGGACATTGACGGTGATGGAAGCTTCATAATG
SEQ ID NO:6   TCTGTGGCGAACCCTGATGCGATTGTTGTGGACATTGACGGTGATGGAAGCTTCATAATG
SEQ ID NO:7   TCTGTGGCGAACCCTGATGCGATTGTTGTGGACATTGACGGTGATGGAAGCTTCATAATG
SEQ ID NO:8   TCTGTGGCGAACCCTGATGCGATTGTTGTGGACATTGACGGTGATGGAAGCTTCATAATG

#1621         ************************************************************
SEQ ID NO:5   AACGTTCAAGAGCTGGCCACAATCCGTGTAGAGAATCTTCCTGTGAAGATACTCTTGTTA
SEQ ID NO:6   AACGTTCAAGAGCTGGCCACAATCCGTGTAGAGAATCTTCCTGTGAAGATACTCTTGTTA
SEQ ID NO:7   AACGTTCAAGAGCTGGCCACAATCCGTGTAGAGAATCTTCCTGTGAAGATACTCTTGTTA
SEQ ID NO:8   AACGTTCAAGAGCTGGCCACAATCCGTGTAGAGAATCTTCCTGTGAAGATACTCTTGTTA

PM2
                                      ↓
         PM2   primer CTTGGGATGGTCATGCAATT   SEQ ID NO:18

WT primer TGGGATGGTCATGCAATG   SEQ ID NO:17
                          ─────────────────▶
#1681         ****************************** ****************************
SEQ ID NO:5   AACAACCAGCATCTTGGGATGGTCATGCAATGGGAAGATCGGTTCTACAAAGCTAACAGA
SEQ ID NO:6   AACAACCAGCATCTTGGGATGGTCATGCAATGGGAAGATCGGTTCTACAAAGCTAACAGA
SEQ ID NO:7   AACAACCAGCATCTTGGGATGGTCATGCAATGGGAAGATCGGTTCTACAAAGCTAACAGA
SEQ ID NO:8   AACAACCAGCATCTTGGGATGGTCATGCAATGGGAAGATCGGTTCTACAAAGCTAACAGA

#1741         ************************************************************
SEQ ID NO:5   GCTCACACTTATCTCGGGGACCCGGCAAGGGAGAACGAGATCTTCCCTAACATGCTGCAG
SEQ ID NO:6   GCTCACACTTATCTCGGGGACCCGGCAAGGGAGAACGAGATCTTCCCTAACATGCTGCAG
SEQ ID NO:7    GCTCACACTTATCTCGGGGACCCGGCAAGGGAGAACGAGATCTTCCCTAACATGCTGCAG
SEQ ID NO:8   GCTCACACTTATCTCGGGGACCCGGCAAGGGAGAACGAGATCTTCCCTAACATGCTGCAG

#1801         ************************************************************
SEQ ID NO:5   TTTGCAGGAGCTTGCGGGATTCCAGCTGCGAGAGTGACGAAGAAAGAAGAACTCCGAGAA
SEQ ID NO:6   TTTGCAGGAGCTTGCGGGATTCCAGCTGCGAGAGTGACGAAGAAAGAAGAACTCCGAGAA
SEQ ID NO:7   TTTGCAGGAGCTTGCGGGATTCCAGCTGCGAGAGTGACGAAGAAAGAAGAACTCCGAGAA
SEQ ID NO:8   TTTGCAGGAGCTTGCGGGATTCCAGCTGCGAGAGTGACGAAGAAAGAAGAACTCCGAGAA
```

Figure 2C

```
                                    PM2 Region Reverse primer
                                         SEQ ID NO:16
                                       ACCTGGCATGGACAACCTA
     #1861                ************************◄─────────************************
     SEQ ID NO:5         GCTATTCAGACAATGCTGGATACACCTGGACCGTACCTGTTGGATGTCATCTGTCCGCAC
     SEQ ID NO:6         GCTATTCAGACAATGCTGGATACACCTGGACCGTACCTGTTGGATGTCATCTGTCCGCAC
     SEQ ID NO:7         GCTATTCAGACAATGCTGGATACACCTGGACCGTACCTGTTGGATGTCATCTGTCCGCAC
     SEQ ID NO:8         GCTATTCAGACAATGCTGGATACACCTGGACCGTACCTGTTGGATGTCATCTGTCCGCAC

#1921               ************************************************************
     SEQ ID NO:5         CAAGAACATGTGTTACCGATGATCCCAAGTGGTGGCACTTTCAAAGATGTAATAACCGAA
     SEQ ID NO:6         CAAGAACATGTGTTACCGATGATCCCAAGTGGTGGCACTTTCAAAGATGTAATAACCGAA
     SEQ ID NO:7         CAAGAACATGTGTTACCGATGATCCCAAGTGGTGGCACTTTCAAAGATGTAATAACCGAA
     SEQ ID NO:8         CAAGAACATGTGTTACCGATGATCCCAAGTGGTGGCACTTTCAAAGATGTAATAACCGAA

#1981               *********************************** .*******************
     SEQ ID NO:5         GGGGATGGTCGCACTAAGTACTGAGAGATGAAGCTGGTGATCCATCATATGGTAAAAGAC
     SEQ ID NO:6         GGGGATGGTCGCACTAAGTACTGAGAGATGAAGCTGGTGATCCATCATATGGTAAAAGAC
     SEQ ID NO:7         GGGGATGGTCGCACTAAGTACTGAGAGATGAAGCTGGTGATCCATCATATGGTAAAAGAC
     SEQ ID NO:8         GGGGATGGTCGCACTAAGTACTGAGAGATGAAGCTGGTGATCCATCATATGGTAAAAGAC

#2041               ************************************************************
     SEQ ID NO:5         TTAGTTTCAGTTTTCAGTTTCTTTTGTGTGGTAATTTGGGTTTGTCAGTTGTTGTACTGC
     SEQ ID NO:6         TTAGTTTCAGTTTTCAGTTTCTTTTGTGTGGTAATTTGGGTTTGTCAGTTGTTGTACTGC
     SEQ ID NO:7         TTAGTTTCAGTTTTCAGTTTCTTTTGTGTGGTAATTTGGGTTTGTCAGTTGTTGTACTGC
     SEQ ID NO:8         TTAGTTTCAGTTTTCAGTTTCTTTTGTGTGGTAATTTGGGTTTGTCAGTTGTTGTACTGC

#2101               ****************. *****************************************
     SEQ ID NO:5         TTTTGGTTTGTTCCCAGAGTTACTCGCTGTTGTTGTTTTGTTTCCTTTTTCTTTTATATA
     SEQ ID NO:6         TTTTGGTTTGTTCCCAGAGTTACTCGCTGTTGTTGTTTTGTTTCCTTTTTCTTTTATATA
     SEQ ID NO:7         TTTTGGTTTGTTCCCAGAGTTACTCGCTGTTGTTGTTTTGTTTCCTTTTTCTTTTATATA
     SEQ ID NO:8         TTTTGGTTTGTTCCCAGATTTACTCGCTGTTGTTGTTTTGTTTCCTTTTTCTTTTATATA
```

Figure 2D

```
SEQ ID NO:19    AGATTCGTTTCTATTCATCCATAATTAATAAAAAAAAAAGACCAAACAAACAAAAATCAT
#-181                                :::  :::::::::::::::::::::::::::::  :::
SEQ ID NO:20                         AAAGAAAAGACCAAACAAACAAAAATCAT

SEQ ID NO:9
                                              ─────────────────────▶
AHAS1 forward amplification primer          CACAAGTCTCGTGTTATAAAA C
                                            ::::::::::::  :::::::: :
SEQ ID NO:19    ATTCCAAGGGTATTTTCGTAAACAAACAAAACCCTCACAAGTCTCGTTTTATAAAA CGA
#-121           :::::::::::::::::::::::::::::::::::::  :::::::::::::: :::
SEQ ID NO:20    ATTCCAAGGGTATTTTCGTAAACAAACAAAACCCTCACAAGCCTCGTTTTATAAAAACGA
                                                 ::::::::::: ::::::::::
AHAS3 forward amplification primer           CACAAGCCTCGTGTTATAAAA
                                              ───────────────────▶
                                                    SEQ ID NO:13

SEQ ID NO:19    TTCACGTTCACAAACTCATTCATCATCTCTCTCCT              CTAACC
#-61            :::::::::::::::::::::::::::::::::::              ::::::
SEQ ID NO:20    TTCACGTTCACAAACTCATTCATCATCTCTCTCTCATTTCTCTCTCTCTCTCATCTAACC

SEQ ID NO:19    ATGGCGGCGGCAACATCGTCTTCTCCGATCTCCTTAACCGCTAAACCTTCTTCCAAATCC
#1              ::::::::::::::::::::::::::::::::::::::::::::::::::::::::::::
SEQ ID NO:20    ATGGCGGCGGCAACATCGTCTTCTCCGATCTCCTTAACCGCTAAACCTTCTTCCAAATCC

SEQ ID NO:19    CCTCTACCCATTTCCAGATTCTCCCTTCCCTTCTCCTTAACCCCACAGAAAGACTCCTCC
#61             :::::::::::::::::::::::::::::::: :::::::::::::::::::  ::::::
SEQ ID NO:20    CCTCTACCCATTTCCAGATTCTCCCTTCCCTTCTCCTTAACCCCACAGAAACCCTCCTCC

SEQ ID NO:19    CGTCTCCACCGTCCTCTCGCCATCTCCGCCGTTCTCAACTCACCCGTCAATGTCGCACCT
#121            :::::::::::::  :::: :::::::::::::::::::::::::::::::::::::
SEQ ID NO:20    CGTCTCCACCGTCCACTCGCCATCTCCGCCGTTCTCAACTCACCCGTCAATGTCGCA

SEQ ID NO:19    CCTTCCCCTGAAAAAACCGACAAGAACAAGACTTTCGTCTCCCGCTACGCTCCCGACGAG
#181                    :::::::::::::::::: :::::::::: :::::::::::::::::::::
SEQ ID NO:20            CCTGAAAAAACCGACAAGATCAAGACTTTCATCTCCCGCTACGCTCCCGACGAG

SEQ ID NO:19    CCCCGCAAGGGTGCTGATATCCTCGTCGAAGCCCTCGAGCGTCAAGGCGTCGAAACCGTC
#241            :::::::::::::::::::::::::::: ::::::::::::::::::::::::::::::
SEQ ID NO:20    CCCCGCAAGGGTGCTGATATCCTCGTGGAAGCCCTCGAGCGTCAAGGCGTCGAAACCGTC

SEQ ID NO:19    TTTGCTTATCCCGGAGGTGCTTCCATGGAGATCCACCAAGCCTTGACTCGCTCCTCCACC
#301            ::  :::::::::::::::::  :::::::::::::::::::::::::: ::::::::::
SEQ ID NO:20    TTCGCTTATCCCGGAGGTGCCTCCATGGAGATCCACCAAGCCTTGACTCGCTCCTCCACC

SEQ ID NO:19    ATCCGTAACGTCCTTCCCCGTCACGAACAAGGAGGAGTCTTCGCCGCCGAGGGTTACGCT
#361            ::::::::::::::::::::::::::::::::::::::::::::::::::::::::::::
SEQ ID NO:20    ATCCGTAACGTCCTCCCCCGTCACGAACAAGGAGGAGTCTTCGCCGCCGAGGGTTACGCT

SEQ ID NO:19    CGTTCCTCCGGCAAACCGGGAATCTGCATAGCCACTTCGGGTCCCGGAGCTACCAACCTC
#421            ::::::::::::::::::::::::::::::::::::::::::::::::::::::::::::
SEQ ID NO:20    CGTTCCTCCGGCAAACCGGGAATCTGCATAGCCACTTCGGGTCCCGGAGCTACCAACCTC

SEQ ID NO:19    GTCAGCGGGTTAGCAGACGCGATGCTTGACAGTGTTCCTCTTGTCGCCATTACAGGACAG
#481            ::::::::::::::: :::::::::::::::::::::::::: :: ::::: ::::::::
SEQ ID NO:20    GTCAGCGGGTTAGCCGACGCGATGCTTGACAGTGTTCCTCTCGTCGCCATCACAGGACAG

SEQ ID NO:19    GTCCCTCGCCGGATGATCGGTACTGACGCCTTCCAAGAGACACCAATCGTTGAGGTAACG
#541            ::::::::::::::::::::::::::: ::::::::::::: ::::::::::::::::::
SEQ ID NO:20    GTCCCTCGCCGGATGATCGGTACTGACGCGTTCCAAGAGACGCCAATCGTTGAGGTAACG

SEQ ID NO:19    AGGTCTATTACGAAACATAACTATTTGGTGATGGATGTTGATGACATACCTAGGATCGTT
#601            :::::::::::::::::::::::: ::::::::::::::::::::::::::::::::::::
SEQ ID NO:20    AGGTCTATTACGAAACATAACTATCTGGTGATGGATGTTGATGACATACCTAGGATCGTT

SEQ ID NO:19    CAAGAAGCTTTCTTTCTAGCTACTTCCGGTAGACCCGGACCGGTTTTGGTTGATGTTCCT
#661            :::::::: ::::::::::::::::::::::::::::::::::::::::::::::::::
SEQ ID NO:20    CAAGAAGCATTCTTTCTAGCTACTTCCGGTAGACCCGGACCGGTTTTGGTTGATGTTCCT
```

Figure 5A

| | |
|---|---|
| SEQ ID NO:19 #721 | AAGGATATTCAGCAGCAGCTTGCGATTCCTAACTGGGATCAACCTATGCGCTTACCTGGC |
| | :::::::::::::::::::::::::::::::::::::::::::::::::::::: :::::: |
| SEQ ID NO:20 | AAGGATATTCAGCAGCAGCTTGCGATTCCTAACTGGGATCAACCTATGCGCTTGCCTGGC |
| SEQ ID NO:19 #781 | TACATGTCTAGGTTGCCTCAGCCTCCGGAAGTTTCTCAGTTAGGTCAGATCGTTAGGTTG |
| | :::::::::::: :::::::::: ::::::::::::::::::::: :::::::::::::::: |
| SEQ ID NO:20 | TACATGTCTAGGCTGCCTCAGCCACCGGAAGTTTCTCAGTTAGGCCAGATCGTTAGGTTG |
| SEQ ID NO:19 #841 | ATCTCGGAGTCTAAGAGGCCTGTTTTGTACGTTGGTGGTGGAAGCTTGAACTCGAGTGAA |
| | :::::::::::::::::::::::::::::::::::::::::::::::::::::::::::: |
| SEQ ID NO:20 | ATCTCGGAGTCTAAGAGGCCTGTTTTGTACGTTGGTGGTGGAAGCTTGAACTCGAGTGAA |
| SEQ ID NO:19 #901 | GAACTGGGGAGATTTGTCGAGCTTACTGGGATCCCCGTTGCGAGTACTTTGATGGGGCTT |
| | ::::::::::::::::::::::::::::::::::::: ::::::::::: :::::::::::: |
| SEQ ID NO:20 | GAACTGGGGAGATTTGTCGAGCTTACTGGGATCCCTGTTGCGAGTACGTTGATGGGGCTT |
| SEQ ID NO:19 #961 | GGCTCTTATCCTTGTAACGATGAGTTGTCCCTGCAGATGCTTGGCATGCACGGGACTGTG |
| | :::::::::::::::::::::::::::::::::::::::::::::::::::::::::::: |
| SEQ ID NO:20 | GGCTCTTATCCTTGTAACGATGAGTTGTCCCTGCAGATGCTTGGCATGCACGGGACTGTG |
| SEQ ID NO:19 #1021 | TATGCTAACTACGCTGTGGAGCATAGTGATTTGTTGCTGGCGTTTGGTGTTAGGTTTGAT |
| | :::::::::::::::::::::::::::::::::::::::::::::::::::::::::::: |
| SEQ ID NO:20 | TATGCTAACTACGCTGTGGAGCATAGTGATTTGTTGCTGGCGTTTGGTGTTAGGTTTGAT |
| SEQ ID NO:19 #1081 | GACCGTGTCACGGGAAAGCTCGAGGCTTTCGCTAGCAGGGCTAAAATTGTGCACATAGAC |
| | ::::::::::::::::::::::::::::: :: :: ::::::::::: ::::::::::::::: |
| SEQ ID NO:20 | GACCGTGTCACGGGAAAGCTCGAGGCGTTTGCGAGCAGGGCTAAGATTGTGCACATAGAC |
| SEQ ID NO:19 #1141 | ATTGATTCTGCTGAGATTGGGAAGAATAAGACACCTCACGTGTCTGTGTGTGGTGATGTA |
| | :::::::::::::::::::::::::::::::::::::::::::::::::::::::::::: |
| SEQ ID NO:20 | ATTGATTCTGCTGAGATTGGGAAGAATAAGACACCTCACGTGTCTGTGTGTGGTGATGTA |
| SEQ ID NO:19 #1201 | AAGCTGGCTTTGCAAGGGATGAACAAGGTTCTTGAGAACCGGGCGGAGGAGCTCAAGCTT |
| | :::::::::::::::::::::::::::::::::::::::::::::::::::::::::::: |
| SEQ ID NO:20 | AAGCTGGCTTTGCAAGGGATGAACAAGGTTCTTGAGAACCGGGCGGAGGAGCTCAAGCTT |
| SEQ ID NO:19 #1261 | GATTTCGGTGTTTGGAGGAGTGAGTTGAGCGAGCAGAAACAGAAGTTCCCTTTGAGCTTC |
| | ::::::::::::::::::::::::::::::::::::::::::::::::: :::::::::: |
| SEQ ID NO:20 | GATTTCGGTGTTTGGAGGAGTGAGTTGAGCGAGCAGAAACAGAAGTTCCCGTTGAGCTTC |
| SEQ ID NO:19 #1321 | AAAACGTTTGGAGAAGCCATTCCTCCGCAGTACGCGATTCAGATCCTCGACGAGCTAACC |
| | ::::::::::::::::::::::::::::::::::::::::::: :::: :::::::::::: |
| SEQ ID NO:20 | AAAACGTTTGGAGAAGCCATTCCTCCGCAGTACGCGATTCAGGTCCTAGACGAGCTAACC |
| SEQ ID NO:19 #1381 | GAAGGGAAGGCAATTATCAGTACTGGTGTTGGACAGCATCAGATGTGGGCGGCGCAGTTT |
| | :::::::::::::::::::::::::::::::::::::::::::::::::::::::::::: |
| SEQ ID NO:20 | CAAGGGAAGGCAATTATCAGTACTGGTGTTGGACAGCATCAGATGTGGGCGGCGCAGTTT |
| SEQ ID NO:19 #1441 | TACAAGTACAGGAAGCCGAGACAGTGGCTGTCGTCATCAGGCCTCGGAGCTATGGGTTTT |
| | :::::::::::::::::::: :::::::::::::::::: ::::: :::::::::::::::: |
| SEQ ID NO:20 | TACAAGTACAGGAAGCCGAGGCAGTGGCTGTCGTCCTCAGGACTCGGAGCTATGGGTTTC |
| SEQ ID NO:19 #1501 | GGACTTCCTGCTGCGATTGGAGCGTCTGTGGCGAACCCTGATGCGATTGTTGTGGATATT |
| | :::::::::::::::::::::::::::::::::::::::::::::::::::::::: ::: |
| SEQ ID NO:20 | GGACTTCCTGCTGCGATTGGAGCGTCTGTGGCGAACCCTGATGCGATTGTTGTGGACATT |
| SEQ ID NO:19 #1561 | GACGGTGATGGAAGCTTCATAATGAACGTTCAAGAGCTGGCCACAATCCGTGTAGAGAAT |
| | :::::::::::::::::::::::::::::::::::::::::::::::::::::::::::: |
| SEQ ID NO:20 | GACGGTGATGGAAGCTTCATAATGAACGTTCAAGAGCTGGCCACAATCCGTGTAGAGAAT |
| SEQ ID NO:19 #1621 | CTTCCTGTGAAGATACTCTTGTTAAACAACCAGCATCTTGGGATGGTCATGCAATGGGAA |
| | :::::::::::::::::::::::::::::::::::::::::::::::::::::::::::: |
| SEQ ID NO:20 | CTTCCTGTGAAGATACTCTTGTTAAACAACCAGCATCTTGGGATGGTCATGCAATGGGAA |
| SEQ ID NO:19 #1681 | GATCGGTTCTACAAAGCTAACAGAGCTCACACTTATCTCGGGGACCCGGCAAGGGAGAAC |
| | :::::::::::::::::::::::::::::::::::::::::::::::::::::::::::: |
| SEQ ID NO:20 | GATCGGTTCTACAAAGCTAACAGAGCTCACACTTATCTCGGGGACCCGGCAAGGGAGAAC |

Figure 5B

```
SEQ ID NO:19      GAGATCTTCCCTAACATGCTGCAGTTTGCAGGAGCTTGCGGGATTCCAGCTGCGAGAGTG
#1741             ::::::::::::::::::::::::::::::::::::::::::::::::::::::::::::
SEQ ID NO:20      GAGATCTTCCCTAACATGCTGCAGTTTGCAGGAGCTTGCGGGATTCCAGCTGCGAGAGTG

SEQ ID NO:19      ACGAAGAAAGAAGAACTCCGAGAAGCTATTCAGACAATGCTGGATACACCAGGACCATAC
#1801             ::::::::::::::::::::::::::::::::::::::::::::::::::::: ::::  :::
SEQ ID NO:20      ACGAAGAAAGAAGAACTCCGAGAAGCTATTCAGACAATGCTGGATACACCTGGACCGTAC

SEQ ID NO:19      CTGTTGGATGTGATATGTCCGCACCAAGAACATGTGTTACCGATGATCCCAAGTGGTGGC
#1861             :::::::::: :: :: ::::::::::::::::::::::::::::::::::::::::::::
SEQ ID NO:20      CTGTTGGATGTCATCTGTCCGCACCAAGAACATGTGTTACCGATGATCCCAAGTGGTGGC

SEQ ID NO:19      ACTTTCAAAGATGTAATAACAGAAGGGGATGGTCGCACTAAGTACTGA|GAGATGAAGCT
#1921             ::::::::::::::::::::: :::::::::::::::::::::::::::|:::::::::::
SEQ ID NO:20      ACTTTCAAAGATGTAATAACCGAAGGGGATGGTCGCACTAAGTACTGA|GAGATGAAGCT

SEQ ID NO:19      GGTGATCGATCATATGGTAAAAGACTTAGTTTCAGTTTCCAGTTTCTTTTGTGTGGTAAT
#1980             :::::: ::::::::::::::::::::::::::::::::: ::::::::::::::::::::
SEQ ID NO:20      GGTGATCCATCATATGGTAAAAGACTTAGTTTCAGTTTTCAGTTTCTTTTGTGTGGTAAT

SEQ ID NO:19      TTGGGTTTGTCAGTTGTTGTACTACTTTTGGTT GTTCCCAGACGTACTCGCTGTTGTTG
#2040             :::::::::::::::::::::::: :::::: :::  :::::::: :::::::::::::::
SEQ ID NO:20      TTGGGTTTGTCAGTTGTTGTACTGCTTTTGGTTTGTTCCCAGACTTACTCGCTGTTGTTG

◄─────────────
AHAS1 reverse amplification                               AAGTAT ACAAA
       Primer                                             :::::  :::::
SEQ ID NO:19      TTTTGTTTCCTTTTTCTTTTATATATAAATAAACTGCTTGGGTTTTTTTTCATA TGTTT
#2100             :::::::::::::::::::::::::::::::::::::::::::::::::: :::  :::::
SEQ ID NO:20      TTTTGTTTCCTTTTTCTTTTATATATAAATAAACTGCTTGGGTTTTTTTACATAATGTTT
AHAS3 reverse amplification                               :::::::::::
       Primer                                             ATGTATTACAAA
                                                          ◄─────────────

AHAS1 rev         CCGTGAGTTAC   SEQ ID NO:10
   Primer         ::  :::::::::
SEQ ID NO:19      GGGACTCAATGCAAGGAA TGCTACTAGACTGCGATTATCTACTAATCTTGCTAGGAAAT
#2160             ::::::::::::::::::: ::::::::::::::::::::::::::::::::::  ::::::
SEQ ID NO:20      GGGACTCAATGCAAGGAAATGCTACTAGACTGCGATTATCTACTAATCTTGCAAGGAAAT
AHAS3 rev         ::  :::::::::
   Primer         CCGTGAGTTAC   SEQ ID NO:14
```

Figure 5C

SEQUENCE LISTING

```
<160> NUMBER OF SEQ ID NOS: 20

<210> SEQ ID NO 1
<211> LENGTH: 2087
<212> TYPE: DNA
<213> ORGANISM: Brassica napus
<220> FEATURE:
<221> NAME/KEY: modified_base
<222> LOCATION: (13)..(14)
<223> OTHER INFORMATION: a, c, g, t, unknown or other
<220> FEATURE:
<221> NAME/KEY: modified_base
<222> LOCATION: (29)..(30)
<223> OTHER INFORMATION: a, c, g, t, unknown or other
<220> FEATURE:
<221> NAME/KEY: modified_base
<222> LOCATION: (34)..(35)
<223> OTHER INFORMATION: a, c, g, t, unknown or other
<220> FEATURE:
<221> NAME/KEY: modified_base
<222> LOCATION: (44)..(45)
<223> OTHER INFORMATION: a, c, g, t, unknown or other
<220> FEATURE:
<221> NAME/KEY: modified_base
<222> LOCATION: (49)..(49)
<223> OTHER INFORMATION: a, c, g, t, unknown or other
<220> FEATURE:
<221> NAME/KEY: modified_base
<222> LOCATION: (51)..(51)
<223> OTHER INFORMATION: a, c, g, t, unknown or other
<220> FEATURE:
<221> NAME/KEY: modified_base
<222> LOCATION: (56)..(56)
<223> OTHER INFORMATION: a, c, g, t, unknown or other
<220> FEATURE:
<221> NAME/KEY: modified_base
<222> LOCATION: (110)..(110)
<223> OTHER INFORMATION: a, c, g, t, unknown or other
<220> FEATURE:
<221> NAME/KEY: modified_base
<222> LOCATION: (657)..(657)
<223> OTHER INFORMATION: a, c, g, t, unknown or other
<220> FEATURE:
<221> NAME/KEY: modified_base
<222> LOCATION: (749)..(749)
<223> OTHER INFORMATION: a, c, g, t, unknown or other

<400> SEQUENCE: 1
gctaaacctt ctnncaaatc ccctctacnn attnncagat tctnncttnc nttctnctta      60
accccacaga aagactcctc ccgtctccac cgtcctctcg ccatctccgn cgttctcaac     120
tcacccgtca atgtcgcacc tccttcccct gaaaaaaccg acaagaacaa gactttcgtc     180
tcccgctacg ctcccgacga gccccgcaag ggtgctgata tcctcgtcga agccctcgag     240
cgtcaaggcg tcgaaaccgt ctttgcttat cccggaggtg cttccatgga gatccaccaa     300
gccttgactc gctcctccac catccgtaac gtccttcccc gtcacgaaca aggaggagtc     360
ttcgccgccg agggttacgc tcgttcctcc ggcaaaccgg gaatctgcat agccacttcg     420
ggtcccggag ctaccaacct cgtcagcggg ttagcagacg cgatgcttga cagtgttcct     480
cttgtcgcca ttcaggaca ggtccctcgc cggatgatcg gtactgacgc cttccaagag     540
acaccaatcg ttgaggtaac gaggtctatt acgaaacata actatttggt gatggatgtt     600
```

```
gatgacatac ctaggatcgt tcaagaagct ttctttctag ctacttccgg tagaccngga    660
ccggttttgg ttgatgttcc taaggatatt cagcagcagc ttgcgattcc taactgggat    720
caacctatgc gcttacctgg ctacatgtnt aggttgcctc agcctccgga agtttctcag    780
ttaggtcaga tcgttaggtt gatctcggag tctaagaggc ctgttttgta cgttggtggt    840
ggaagcttga actcgagtga agaactgggg agatttgtcg agcttactgg gatccccgtt    900
gcgagtactt tgatggggct tggctcttat ccttgtaacg atgagttgtc cctgcagatg    960
cttggcatgc acgggactgt gtatgctaac tacgctgtgg agcatagtga tttgttgctg   1020
gcgtttggtg ttaggtttga tgaccgtgtc acgggaaagc tcgaggcttt cgctagcagg   1080
gctaaaattg tgcacataga cattgattct gctgagattg ggaagaataa gacacctcac   1140
gtgtctgtgt gtggtgatgt aaagctggct ttgcaaggga tgaacaaggt tcttgagaac   1200
cgggcggagg agctcaagct tgatttcggt gtttggagga gtgagttgag cgagcagaaa   1260
cagaagttcc ctttgagctt caaaacgttt ggagaagcca ttcctccgca gtacgcgatt   1320
cagatcctcg acgagctaac cgaagggaag gcaattatca gtactggtgt tggacagcat   1380
cagatgtggg cggcgcagtt ttacaagtac aggaagccga acagtggct gtcgtcatca    1440 ggcctcggag ctatgggttt tggacttcct gctgcgattg gagcgtctgt ggcgaaccct   1500
gatgcgattg ttgtggatat tgacggtgat ggaagcttca taatgaacgt tcaagagctg   1560
gccacaatcc gtgtagagaa tcttcctgtg aagatactct tgttaaacaa ccagcatctt   1620
gggatggtca tgcaatggga agatcggttc tacaaagcta acagagctca cacttatctc   1680
ggggacccgg caagggagaa cgagatcttc cctaacatgc tgcagtttgc aggagcttgc   1740
gggattccag ctgcgagagt gacgaagaaa gagaactcc gagaagctat tcagacaatg    1800
ctggatacac caggaccata cctgttggat gtgatatgtc cgcaccaaga acatgtgtta   1860
ccgatgatcc caaatggtgg cactttcaaa gatgtaataa cagaaggga tggtcgcact    1920 aagtactgag agatgaagct ggtgatcgat catatggtaa aagacttagt ttcagtttcc   1980
agtttctttt gtgtggtaat ttgggtttgt cagttgttgt actactttg gttgttccca    2040 gacgtactcg ctgttgttgt tttgtttcct tttctcttta tatataa                 2087
```

```
<210> SEQ ID NO 2
<211> LENGTH: 2003
<212> TYPE: DNA
<213> ORGANISM: Brassica napus
<220> FEATURE:
<221> NAME/KEY: modified_base
<222> LOCATION: (25)..(25)
<223> OTHER INFORMATION: a, c, g, t, unknown or other
<220> FEATURE:
<221> NAME/KEY: modified_base
<222> LOCATION: (64)..(64)
<223> OTHER INFORMATION: a, c, g, t, unknown or other
<220> FEATURE:
<221> NAME/KEY: modified_base
<222> LOCATION: (98)..(98)
<223> OTHER INFORMATION: a, c, g, t, unknown or other
<220> FEATURE:
<221> NAME/KEY: modified_base
<222> LOCATION: (1628)..(1628)
<223> OTHER INFORMATION: a, c, g, t, unknown or other
<220> FEATURE:
<221> NAME/KEY: modified_base
<222> LOCATION: (1698)..(1698)
<223> OTHER INFORMATION: a, c, g, t, unknown or other
<220> FEATURE:
<221> NAME/KEY: modified_base
<222> LOCATION: (1719)..(1719)
<223> OTHER INFORMATION: a, c, g, t, unknown or other
```

```
<220> FEATURE:
<221> NAME/KEY: modified_base
<222> LOCATION: (1733)..(1733)
<223> OTHER INFORMATION: a, c, g, t, unknown or other
<220> FEATURE:
<221> NAME/KEY: modified_base
<222> LOCATION: (1969)..(1969)
<223> OTHER INFORMATION: a, c, g, t, unknown or other

<400> SEQUENCE: 2
gtctccaccg tcctctcgcc atctncgccg ttctcaactc acccgtcaat gtcgcacctc      60
cttnccctga aaaaaccgac aagaacaaga ctttcgtntc ccgctacgct cccgacgagc     120
cccgcaaggg tgctgatatc ctcgtcgaag ccctcgagcg tcaaggcgtc gaaaccgtct     180
ttgcttatcc cggaggtgct tccatggaga tccaccaagc cttgactcgc tcctccacca     240
tccgtaacgt ccttcccgt cacgaacaag gaggagtctt cgccgccgag ggttacgctc     300
gttcctccgg caaaccggga atctgcatag ccacttcggg tcccggagct accaacctcg     360
tcagcgggtt agcagacgcg atgcttgaca gtgttcctct tgtcgccatt acaggacagg     420
tccctcgccg gatgatcggt actgacgcct tccaagagac accaatcgtt gaggtaacga     480
ggtctattac gaaacataac tatttggtga tggatgttga tgacataacct aggatcgttc     540
aagaagcttt ctttctagct acttccggta gacccggacc ggttttggtt gatgttccta     600
aggatattca gcagcagctt gcgattccta actgggatca acctatgcgc ttacctggct     660
acatgtctag gttgcctcag cctccggaag tttctcagtt aggtcagatc gttaggttga     720
tctcggagtc taagaggcct gttttgtacg ttggtggtgg aagcttgaac tcgagtgaag     780
aactggggag atttgtcgag cttactggga tccccgttgc gagtactttg atggggcttg     840
gctcttatcc ttgtaacgat gagttgtccc tgcagatgct tggcatgcac gggactgtgt     900
atgctaacta cgctgtggag catagtgatt tgttgctggc gtttggtgtt aggtttgatg     960
accgtgtcac gggaaagctc gaggcttccg ctagcagggc taaaattgtg cacatagaca    1020
ttgattctgc tgagattggg aagaataaga cacctcacgt gtctgtgtgt ggtgatgtaa    1080
agctggcttt gcaagggatg aacaaggttc ttgagaaccg ggcggaggag ctcaagcttg    1140
atttcggtgt ttggaggagt gagttgagcg agcagaaaca gaagttccct ttgagcttca    1200
aaacgtttgg agaagccatt cctccgcagt acgcgattca gatcctcgac gagctaaccg    1260
aagggaaggc aattatcagt actggtgttg gacagcatca gatgtgggcg cgcagttttt    1320
acaagtacag gaagccgaga cagtggctgt cgtcatcagg cctcggagct atgggttttg    1380
gacttcctgc tgcgattgga gcgtctgtgg cgaaccctga tgcgattgtt gtggatattg    1440
acggtgatgg aagcttcata atgaacgttc aagagctggc cacaatccgt gtagagaatc    1500
ttcctgtgaa gatactcttg ttaaacaacc agcatcttgg gatggtcatg caatgggaag    1560
atcggttcta caaagctaac agagctcaca cttatctcgg ggacccggca agggagaacg    1620
agatcttncc taacatgctg cagtttgcag gagcttgcgg gattccagct gcgagagtga    1680
cgaagaaaga agaactcnga gaagctattc agacaatgnt ggatacacca ggnccatacc    1740
tgttggatgt gatatgtccg caccaagaac atgtgttacc gatgatccca agtggtggca    1800
cttttcaaga tgtaataaca gaaggggatg gtcgcactaa gtactgagag atgaagctgg    1860
tgatcgatca tatggtaaaa gacttagttt cagtttccag tttcttttgt gtggtaattt    1920
gggtttgtca gttgttgtac tacttttggt tgttcccaga cgtactcgnt gttgttgttt    1980
tgtttccttt ttctttata tat                                             2003
```

<210> SEQ ID NO 3
<211> LENGTH: 2077
<212> TYPE: DNA
<213> ORGANISM: Brassica napus
<220> FEATURE:
<221> NAME/KEY: modified_base
<222> LOCATION: (74)..(74)
<223> OTHER INFORMATION: a, c, g, t, unknown or other
<220> FEATURE:
<221> NAME/KEY: modified_base
<222> LOCATION: (83)..(83)
<223> OTHER INFORMATION: a, c, g, t, unknown or other
<220> FEATURE:
<221> NAME/KEY: modified_base
<222> LOCATION: (97)..(97)
<223> OTHER INFORMATION: a, c, g, t, unknown or other
<220> FEATURE:
<221> NAME/KEY: modified_base
<222> LOCATION: (103)..(103)
<223> OTHER INFORMATION: a, c, g, t, unknown or other
<220> FEATURE:
<221> NAME/KEY: modified_base
<222> LOCATION: (118)..(118)
<223> OTHER INFORMATION: a, c, g, t, unknown or other
<220> FEATURE:
<221> NAME/KEY: modified_base
<222> LOCATION: (1035)..(1035)
<223> OTHER INFORMATION: a, c, g, t, unknown or other

<400> SEQUENCE: 3

```
ttcttccaaa tcccctctac ccatttccag attctcccct cccttctcct taaccccaca      60
gaaagactcc tccngtctcc acngtcctct cgccatntcc gcngttctca actcaccngt     120
caatgtcgca cctccttccc ctgaaaaaac cgacaagaac aagactttcg tctcccgcta     180
cgctcccgac gagccccgca agggtgctga tatcctcgtc gaagccctcg agcgtcaagg     240
cgtcgaaacc gtctttgctt atcccggagg tgcttccatg gagatccacc aagccttgac     300
tcgctcctcc accatccgta acgtccttcc ccgtcacgaa caaggaggag tcttcgccgc     360
cgagggttac gctcgttcct ccggcaaacc gggaatctgc atagccactt cgggtcccgg     420
agctaccaac ctcgtcagcg ggttagcaga cgcgatgctt gacagtgttc ctcttgtcgc     480
cattacagga caggtccctc gccggatgat cggtactgac gccttccaag agacaccaat     540
cgttgaggta acgaggtcta ttacgaaaca taactatttg gtgatggatg ttgatgacat     600
acctaggatc gttcaagaag cttttctttct agctacttcc ggtagacccg gaccggtttt     660
ggttgatgtt cctaaggata ttcagcagca gcttgcgatt cctaactggg atcaacctat     720
gcgcttacct ggctacatgt ctaggttgcc tcagcctccg gaagtttctc agttaggtca     780
gatcgttagg ttgatctcgg agtctaagag gcctgttttg tacgttggtg gtggaagctt     840
gaactcgagt gaagaactgg ggagatttgt cgagcttact gggatccccg ttgcgagtac     900
tttgatgggg cttggctctt atccttgtaa cgatgagttg tccctgcaga tgcttggcat     960
gcacgggact gtgtatgcta actacgctgt ggagcatagt gatttgttgc tggcgttttgg    1020
tgttaggttt gatgnccgtg tcacgggaaa gctcgaggct ttcgctagca gggctaaaat    1080
tgtgcacata gacattgatt ctgctgagat tgggaagaat aagacacctc acgtgtctgt    1140
gtgtggtgat gtaaagctgg cttttgcaagg gatgaacaag gttcttgaga accgggcgga    1200
ggagctcaag cttgatttcg tgtttggag gagtgagttg agcgagcaga aacagaagtt    1260
cccctttgagc ttcaaaacgt ttggagaagc cattcctccg cagtacgcga ttcagatcct    1320
cgacgagcta accgaaggga aggcaattat cagtactggt gttggacagc atcagatgtg    1380
ggcggcgcag ttttacaagt acaggaagcc gagacagtgg ctgtcgtcat caggcctcgg    1440
```

-continued

```
agctatgggt tttggacttc ctgctgcgat tggagcgtct gtggcgaacc ctgatgcgat    1500
tgttgtggat attgacggtg atggaagctt cataatgaac gttcaagagc tggccacaat    1560
ccgtgtagag aatcttcctg tgaagatact cttgttaaac aaccagcatc ttgggatggt    1620
catgcaatgg gaagatcggt tctacaaagc taacagagct cacacttatc tcggggaccc    1680
ggcaagggag aacgagatct tccctaacat gctgcagttt gcaggagctt gcgggattcc    1740
agctgcgaga gtgacgaaga agaagaact ccgagaagct attcagacaa tgctggatac     1800
accaggacca tacctgttgg atgtgatatg tccgcaccaa gaacatgtgt taccgatgat    1860
cccaaatggt ggcactttca agatgtaat aacagaaggg gatggtcgca ctaagtactg     1920
agagatgaag ctggtgatcg atcatatggt aaaagactta gtttcagttt ccagtttctt    1980
ttgtgtggta atttgggttt gtcagttgtt gtactacttt tggttgttcc cagacgtact    2040
cgctgttgtt gttttgtttc cttttctctt tatatat                             2077
```

<210> SEQ ID NO 4
<211> LENGTH: 1990
<212> TYPE: DNA
<213> ORGANISM: Brassica napus
<220> FEATURE:
<221> NAME/KEY: modified_base
<222> LOCATION: (2)..(2)
<223> OTHER INFORMATION: a, c, g, t, unknown or other
<220> FEATURE:
<221> NAME/KEY: modified_base
<222> LOCATION: (8)..(8)
<223> OTHER INFORMATION: a, c, g, t, unknown or other
<220> FEATURE:
<221> NAME/KEY: modified_base
<222> LOCATION: (29)..(29)
<223> OTHER INFORMATION: a, c, g, t, unknown or other
<220> FEATURE:
<221> NAME/KEY: modified_base
<222> LOCATION: (32)..(32)
<223> OTHER INFORMATION: a, c, g, t, unknown or other
<220> FEATURE:
<221> NAME/KEY: modified_base
<222> LOCATION: (80)..(80)
<223> OTHER INFORMATION: a, c, g, t, unknown or other
<220> FEATURE:
<221> NAME/KEY: modified_base
<222> LOCATION: (89)..(89)
<223> OTHER INFORMATION: a, c, g, t, unknown or other
<220> FEATURE:
<221> NAME/KEY: modified_base
<222> LOCATION: (98)..(98)
<223> OTHER INFORMATION: a, c, g, t, unknown or other
<220> FEATURE:
<221> NAME/KEY: modified_base
<222> LOCATION: (652)..(652)
<223> OTHER INFORMATION: a, c, g, t, unknown or other
<220> FEATURE:
<221> NAME/KEY: modified_base
<222> LOCATION: (1350)..(1350)
<223> OTHER INFORMATION: a, c, g, t, unknown or other

<400> SEQUENCE: 4

```
tngccatntc cgccgttctc aactcaccng tnaatgtcgc acctccttcc cctgaaaaaa    60
ccgacaagaa caagactttn gtctcccgnt acgctccnga cgagccccgc aagggtgctg    120
atatcctcgt cgaagccctc gagcgtcaag gcgtcgaaac cgtctttgct tatcccggag    180
gtgcttccat ggagatccac caagccttga ctcgctcctc caccatccgt aacgtccttc    240
cccgtcacga acaaggagga gtcttcgccg ccgagggtta cgctcgttcc tccggcaaac    300
cgggaatctg catagccact tcgggtcccg gagctaccaa cctcgtcagc gggttagcag    360
```

```
acgcgatgct tgacagtgtt cctcttgtcg ccattacagg acaggtccct cgccggatga    420
tcggtactga cgccttccaa gagacaccaa tcgttgaggt aacgaggtct attacgaaac    480
ataactattt ggtgatggat gttgatgaca tacctaggat cgttcaagaa gctttctttc    540
tagctacttc cggtagaccc ggaccggttt tggttgatgt tcctaaggat attcagcagc    600
agcttgcgat tcctaactgg gatcaaccta tgcgcttacc tggctacatg tntaggttgc    660
ctcagcctcc ggaagtttct cagttaggtc agatcgttag gttgatctcg gagtctaaga    720
ggcctgtttt gtacgttggt ggtggaagct tgaactcgag tgaagaactg gggagatttg    780
tcgagcttac tgggatcccc gttgcgagta ctttgatggg gcttggctct tatccttgta    840
acgatgagtt gtccctgcag atgcttggca tgcacgggac tgtgtatgct aactacgctg    900
tggagcatag tgatttgttg ctggcgtttg gtgttaggtt tgatgaccgt gtcacgggaa    960
agctcgaggc tttcgctagc agggctaaaa ttgtgcacat agacattgat tctgctgaga    1020
ttgggaagaa taagacacct cacgtgtctg tgtgtggtga tgtaaagctg gctttgcaag    1080
ggatgaacaa ggttcttgag aacgggcgg aggagctcaa gcttgatttc ggtgtttgga    1140
ggagtgagtt gagcgagcag aaacagaagt tcccctttgag cttcaaaacg tttggagaag    1200
ccattcctcc gcagtacgcg attcagatcc tcgacgagct aaccgaaggg aaggcaatta    1260
tcagtactgg tgttggacag catcagatgt gggcggcgca gttttacaag tacaggaagc    1320
cgagacagtg gctgtcgtca tcaggcctcn gagctatggg ttttggactt cctgctgcga    1380
ttggagcgtc tgtggcgaac cctgatgcga ttgttgtgga tattgacggt gatggaagct    1440
tcataatgaa cgttcaagag ctggccacaa tccgtgtaga gaatcttcct gtgaagatac    1500
tcttgttaaa caaccagcat cttgggatgg tcatgcaatg ggaagatcgg ttctacaaag    1560
ctaacagagc tcacacttat ctcggggacc cggcaaggga gaacgagatc ttccctaaca    1620
tgctgcagtt tgcaggagct tgcgggattc cagctgcgag agtgacgaag aaagaagaac    1680
tccgagaagc tattcagaca atgctggata caccaggacc atacctgttg gatgtgatat    1740
gtccgcacca agaacatgtg ttaccgatga tcccaagtgg tggcactttc aaagatgtaa    1800
taacagaagg ggatggtcgc actaagtact gagagatgaa gctggtgatc gatcatatgg    1860
taaaagactt agtttcagtt tccagttct tttgtgtggt aatttgggtt tgtcagttgt    1920
tgtactactt ttggttgttc ccagacgtac tcgctgttgt tgttttgttt cctttttctt    1980
ttatatataa                                                           1990

<210> SEQ ID NO 5
<211> LENGTH: 2025
<212> TYPE: DNA
<213> ORGANISM: Brassica napus
<220> FEATURE:
<221> NAME/KEY: modified_base
<222> LOCATION: (31)..(31)
<223> OTHER INFORMATION: a, c, g, t, unknown or other
<220> FEATURE:
<221> NAME/KEY: modified_base
<222> LOCATION: (709)..(709)
<223> OTHER INFORMATION: a, c, g, t, unknown or other
<220> FEATURE:
<221> NAME/KEY: modified_base
<222> LOCATION: (979)..(979)
<223> OTHER INFORMATION: a, c, g, t, unknown or other
<220> FEATURE:
<221> NAME/KEY: modified_base
<222> LOCATION: (990)..(1273)
<223> OTHER INFORMATION: a, c, g, t, unknown or other

<400> SEQUENCE: 5
```

```
ttctccttaa ccccacagaa accctcctcc ngtctccacc gtccactcgc catctccgcc    60
gttctcaact cacccgtcaa tgtcgcacct gaaaaaaccg acaagatcaa gactttcatc   120
tcccgctacg ctcccgacga gccccgcaag ggtgctgata tcctcgtgga agccctcgag   180
cgtcaaggcg tcgaaaccgt cttcgcttat cccggaggtg cctccatgga gatccaccaa   240
gccttgactc gctcctccac catccgtaac gtcctccccc gtcacgaaca aggaggagtc   300
ttcgccgccg agggttacgc tcgttcctcc ggcaaaccgg aatctgcat agccacttcg    360 ggtcccggag ctaccaacct cgtcagcggg ttagccgacg cgatgcttga cagtgttcct   420
ctcgtcgcca tcacaggaca ggtccctcgc cggatgatcg gtactgacgc gttccaagag   480
acgccaatcg ttgaggtaac gaggtctatt acgaaacata actatctggt gatggatgtt   540
gatgacatac ctaggatcgt tcaagaagca ttctttctag ctacttccgg tagacccgga   600
ccggttttgg ttgatgttcc taaggatatt cagcagcagc ttgcgattcc taactgggat   660
caacctatgc gcttgcctgg ctacatgtct aggctgcctc agccaccgna agtttctcag   720
ttaggccaga tcgttaggtt gatctcggag tctaagaggc ctgttttgta cgttggtggt   780
ggaagcttga actcgagtga agaactgggg agatttgtcg agcttactgg gatccctgtt   840
gcgagtacgt tgatggggct tggctcttat ccttgtaacg atgagttgtc cctgcagatg   900
cttggcatgc acgggactgt gtatgctaac tacgctgtgg agcatagtga tttgttgctg   960
gcgtttggtg ttaggtttna tgaccgtgtn nnnnnnnnnn nnnnnnnnnn nnnnnnnnnn  1020
nnnnnnnnnn nnnnnnnnnn nnnnnnnnnn nnnnnnnnnn nnnnnnnnnn nnnnnnnnnn  1080
nnnnnnnnnn nnnnnnnnnn nnnnnnnnnn nnnnnnnnnn nnnnnnnnnn nnnnnnnnnn  1140
nnnnnnnnnn nnnnnnnnnn nnnnnnnnnn nnnnnnnnnn nnnnnnnnnn nnnnnnnnnn  1200
nnnnnnnnnn nnnnnnnnnn nnnnnnnnnn nnnnnnnnnn nnnnnnnnnn nnnnnnnnnn  1260
nnnnnnnnnn nnnagctaac ccaagggaag gcaattatca gtactggtgt tggacagcat  1320
cagatgtggg cggcgcagtt ttacaagtac aggaagccga ggcagtggct gtcgtcctca  1380
ggactcggag ctatgggttt cggacttcct gctgcgattg gagcgtctgt ggcgaaccct  1440
gatgcgattg ttgtggacat tgacggtgat ggaagcttca taatgaacgt tcaagagctg  1500
gccacaatcc gtgtagagaa tcttcctgtg aagatactct tgttaaacaa ccagcatctt  1560
gggatggtca tgcaatggga agatcggttc tacaaagcta acagagctca cacttatctc  1620
ggggacccgg caagggagaa cgagatcttc cctaacatgc tgcagtttgc aggagcttgc  1680
gggattccag ctgcgagagt gacgaagaaa gaagaactcc gagaagctat tcagacaatg  1740
ctggatacac ctggaccgta cctgttggat gtcatctgtc cgcaccaaga acatgtgtta  1800
ccgatgatcc caagtggtgg cactttcaaa gatgtaataa ccgaagggga tggtcgcact  1860
aagtactgag agatgaagct ggtgatccat catatggtaa aagacttagt ttcagttttc  1920
agtttctttt gtgtggtaat ttgggtttgt cagttgttgt actgcttttg gtttgttccc  1980
agacttactc gctgttgttg ttttgtttcc tttttctttt atata              2025
```

<210> SEQ ID NO 6
<211> LENGTH: 2160
<212> TYPE: DNA
<213> ORGANISM: Brassica napus

<400> SEQUENCE: 6

```
tcattcatca tctctctctc atttctctct ctctctcatc taaccatggc ggcggcaaca    60
```

```
tcgtcttctc cgatctcctt aaccgctaaa ccttcttcca aatccctct acccatttcc    120 agattctccc ttcccttctc cttaacccca cagaaaccct cctcccgtct ccaccgtcca    180
ctcgccatct ccgccgttct caactcaccc gtcaatgtcg cacctgaaaa aaccgacaag    240
atcaagactt tcatctcccg ctacgctccc gacgagcccc gcaagggtgc tgatatcctc    300
gtggaagccc tcgagcgtca aggcgtcgaa accgtcttcg cttatcccgg aggtgcctcc    360
atggagatcc accaagcctt gactcgctcc tccaccatcc gtaacgtcct cccccgtcac    420
gaacaaggag gagtcttcgc cgccgagggt tacgctcgtt cctccggcaa accgggaatc    480
tgcatagcca cttcgggtcc cggagctacc aacctcgtca gcgggttagc cgacgcgatg    540
cttgacagtg ttcctctcgt cgccatcaca ggacaggtcc ctcgccggat gatcggtact    600
gacgcgttcc aagagacgcc aatcgttgag gtaacgaggt ctattacgaa acataactat    660
ctggtgatgg atgttgatga catacctagg atcgttcaag aagcattctt tctagctact    720
tccggtagac ccggaccggt tttggttgat gttcctaagg atattcagca gcagcttgcg    780
attcctaact gggatcaacc tatgcgcttg cctggctaca tgtctaggct gcctcagcca    840
ccggaagttt ctcagttagg ccagatcgtt aggttgatct cggagtctaa gaggcctgtt    900
ttgtacgttg gtggtggaag cttgaactcg agtgaagaac tggggagatt tgtcgagctt    960
actgggatcc ctgttgcgag tacgttgatg gggcttggct cttatccttg taacgatgag    1020
ttgtccctgc agatgcttgg catgcacggg actgtgtatg ctaactacgc tgtggagcat    1080
agtgatttgt tgctggcgtt tggtgttagg tttgatgacc gtgtcacggg aaagctcgag    1140
gcgtttgcga gcagggctaa gattgtgcac atagacattg attctgctga gattgggaag    1200
aataagacac ctcacgtgtc tgtgtgtggt gatgtaaagc tggctttgca agggatgaac    1260
aaggttcttg agaaccgggc ggaggagctc aagcttgatt tcggtgtttg gaggagtgag    1320
ttgagcgagc agaaacagaa gttcccgttg agcttcaaaa cgtttggaga agccattcct    1380
ccgcagtacg cgattcaggt cctagacgag ctaacccaag ggaaggcaat tatcagtact    1440
ggtgttggac agcatcagat gtgggcggcg cagttttaca agtacaggaa gccgaggcag    1500
tggctgtcgt cctcaggact cggagctatg ggtttcggac ttcctgctgc gattggagcg    1560
tctgtggcga accctgatgc gattgttgtg gacattgacg gtgatggaag cttcataatg    1620
aacgttcaag agctggccac aatccgtgta gagaatcttc ctgtgaagat actcttgtta    1680
aacaaccagc atcttgggat ggtcatgcaa ttggaagatc ggttctacaa agctaacaga    1740
gctcacactt atctcgggga cccggcaagg gagaacgaga tcttccctaa catgctgcag    1800
tttgcaggag cttgcgggat tccagctgcg agagtgacga agaaagaaga actccgagaa    1860
gctattcaga caatgctgga tacacctgga ccgtacctgt tggatgtcat ctgtccgcac    1920
caagaacatg tgttaccgat gatcccaagt ggtggcactt tcaaagatgt aataaccgaa    1980
ggggatggtc gcactaagta ctgagagatg aagctggtga tccatcatat ggtaaaagac    2040
ttagtttcag tttttcagttt cttttgtgtg gtaatttggg tttgtcagtt gttgtactgc    2100
ttttggtttg ttcccagact tactcgctgt tgttgttttg tttccttttt cttttatata    2160
```

<210> SEQ ID NO 7
<211> LENGTH: 1994
<212> TYPE: DNA
<213> ORGANISM: Brassica napus
<220> FEATURE:
<221> NAME/KEY: modified_base
<222> LOCATION: (9)..(9)
<223> OTHER INFORMATION: a, c, g, t, unknown or other

```
<220> FEATURE:
<221> NAME/KEY: modified_base
<222> LOCATION: (23)..(23)
<223> OTHER INFORMATION: a, c, g, t, unknown or other
<220> FEATURE:
<221> NAME/KEY: modified_base
<222> LOCATION: (95)..(95)
<223> OTHER INFORMATION: a, c, g, t, unknown or other
<220> FEATURE:
<221> NAME/KEY: modified_base
<222> LOCATION: (678)..(678)
<223> OTHER INFORMATION: a, c, g, t, unknown or other

<400> SEQUENCE: 7
```

| | | | | | |
|---|---|---|---|---|---|
| gtctccacng | tccactcgcc | atntccgccg | ttctcaactc | acccgtcaat | gtcgcacctg | 60 |
| aaaaaaccga | caagatcaag | actttcatct | cccgntacgc | tcccgacgag | ccccgcaagg | 120 |
| gtgctgatat | cctcgtggaa | gccctcgagc | gtcaaggcgt | cgaaaccgtc | ttcgcttatc | 180 |
| ccggaggtgc | ctccatggag | atccaccaag | ccttgactcg | ctcctccacc | atccgtaacg | 240 |
| tcctcccccg | tcacgaacaa | ggaggagtct | tcgccgccga | gggttacgct | cgttcctccg | 300 |
| gcaaaccggg | aatctgcata | gccacttcgg | gtcccggagc | taccaacctc | gtcagcgggt | 360 |
| tagccgacgc | gatgcttgac | agtgttcctc | tcgtcgccat | cacaggacag | gtccctcgcc | 420 |
| ggatgatcgg | tactgacgcg | ttccaagaga | cgccaatcgt | tgaggtaacg | aggtctatta | 480 |
| cgaaacataa | ctatctggtg | atggatgttg | atgacatacc | taggatcgtt | caagaagcat | 540 |
| tctttctagc | tacttccggt | agacccggac | cggttttggt | tgatgttcct | aaggatattc | 600 |
| agcagcagct | tgcgattcct | aactgggatc | aacctatgcg | cttgcctggc | tacatgtcta | 660 |
| ggctgcctca | gccaccgnaa | gtttctcagt | taggccagat | cgttaggttg | atctcggagt | 720 |
| ctaagaggcc | tgttttgtac | gttggtggtg | gaagcttgaa | ctcgagtgaa | gaactgggga | 780 |
| gatttgtcga | gcttactggg | atccctgttg | cgagtacgtt | gatggggctt | ggctcttatc | 840 |
| cttgtaacga | tgagttgtcc | ctgcagatgc | ttggcatgca | cgggactgtg | tatgctaact | 900 |
| acgctgtgga | gcatagtgat | ttgttgctgg | cgtttggtgt | taggtttgat | gaccgtgtca | 960 |
| cgggaaagct | cgaggcgttt | gcgagcaggg | ctaagattgt | gcacatagac | attgattctg | 1020 |
| ctgagattgg | gaagaataag | acacctcacg | tgtctgtgtg | tggtgatgta | aagctggctt | 1080 |
| tgcaagggat | gaacaaggtt | cttgagaacc | gggcggagga | gctcaagctt | gatttcggtg | 1140 |
| tttggaggag | tgagttgagc | gagcagaaac | agaagttccc | gttgagcttc | aaaacgtttg | 1200 |
| gagaagccat | tcctccgcag | tacgcgattc | aggtcctaga | cgagctaacc | caagggaagg | 1260 |
| caattatcag | tactggtgtt | ggacagcatc | agatgtgggc | ggcgcagttt | acaagtaca | 1320 |
| ggaagccgag | gcagtggctg | tcgtcctcag | gactcggagc | tatgggtttc | ggacttcctg | 1380 |
| ctgcgattgg | agcgtctgtg | gcgaaccctg | atgcgattgt | tgtggacatt | gacggtgatg | 1440 |
| gaagcttcat | aatgaacgtt | caagagctgg | ccacaatccg | tgtagagaat | cttcctgtga | 1500 |
| agatactctt | gttaaacaac | cagcatcttg | ggatggtcat | gcaattggaa | gatcggttct | 1560 |
| acaaagctaa | cagagctcac | acttatctcg | ggacccggc | aagggagaac | gagatcttcc | 1620 |
| ctaacatgct | gcagttttca | ggagcttgcg | ggattccagc | tgcgagagtg | acgaagaaag | 1680 |
| aagaactccg | agaagctatt | cagacaatgc | tggatacacc | tggaccgtac | ctgttggatg | 1740 |
| tcatctgtcc | gcaccaagaa | catgtgttac | cgatgatccc | aagtggtggc | actttcaaag | 1800 |
| atgtaataac | cgaaggggat | ggtcgcacta | agtactgaga | gatgaagctg | gtgatccatc | 1860 |
| atatggtaaa | agacttagtt | tcagttttca | gtttcttttg | tgtggtaatt | tgggtttgtc | 1920 |

```
agttgttgta ctgcttttgg tttgttccca gacttactcg ctgttgttgt tttgtttcct    1980 tttctttta tata                                                      1994

<210> SEQ ID NO 8
<211> LENGTH: 1950
<212> TYPE: DNA
<213> ORGANISM: Brassica napus
<220> FEATURE:
<221> NAME/KEY: modified_base
<222> LOCATION: (51)..(51)
<223> OTHER INFORMATION: a, c, g, t, unknown or other
<220> FEATURE:
<221> NAME/KEY: modified_base
<222> LOCATION: (634)..(634)
<223> OTHER INFORMATION: a, c, g, t, unknown or other
<220> FEATURE:
<221> NAME/KEY: modified_base
<222> LOCATION: (996)..(996)
<223> OTHER INFORMATION: a, c, g, t, unknown or other

<400> SEQUENCE: 8
gtcaatgtcg cacctgaaaa aaccgacaag atcaagactt tcatctcccg ntacgctccc      60
gacgagcccc gcaagggtgc tgatatcctc gtggaagccc tcgagcgtca aggcgtcgaa     120
accgtcttcg cttatcccgg aggtgcttcc atggagatcc accaagcctt gactcgctcc     180
tccaccatcc gtaacgtcct ccccgtcac gaacaaggag gagtcttcgc cgccgagggt      240
tacgctcgtt cctccggcaa accgggaatc tgcatagcca cttcgggtcc cggagctacc     300
aacctcgtca gcgggttagc cgacgcgatg cttgacagtg ttcctctcgt cgccatcaca     360
ggacaggtcc ctcgccggat gatcggtact gacgcgttcc aagagacgcc aatcgttgag     420
gtaacgaggt ctattacgaa acataactat ctggtgatgg atgttgatga catacctagg     480
atcgttcaag aagcttttctt tctagctact tccggtagac ccggaccggt tttggttgat     540
gttcctaagg atattcagca gcagcttgcg attcctaact gggatcaacc tatgcgcttg     600
cctggctaca tgtctaggct gcctcagcca ccgnaagttt tcagttagg tcagatcgtt      660 aggttgatct cggagtctaa gaggcctgtt ttgtacgttg gtggtggaag cttgaactcg     720
agtgaagaac tggggagatt tgtcgagctt actgggatcc ctgttgcgag tacgttgatg     780
gggcttggct cttatccttg taacgatgac ttgtccctgc agatgcttgg catgcacggg     840
actgtgtatg ctaactacgc tgtggagcat agtgatttgt tgctggcgtt tggtgttagg     900
tttgatgacc gtgtcacggg aaagctcgag gcgtttgcga gcagggctaa gattgtgcac     960
atagacattg attctgctga gattgggaag aataanacac ctcacgtgtc tgtgtgtggt    1020
gatgtaaagc tggctttgca agggatgaac aaggttcttg agaaccgggc ggaggagctc    1080
aagcttgatt tcggtgtttg gaggagtgag ttgagcgagc agaaacagaa gttcccgttg    1140
agcttcaaaa cgtttggaga agccattcct ccgcagtacg cgattcaggt cctagacgag    1200
ctaacccaag ggaaggcaat tatcagtact ggtgttggac agcatcagat gtgggcggcg    1260
cagttttaca agtacaggaa gccgaggcag tggctgtcgt cctcaggact cggagctatg    1320
ggtttcggac ttcctgctgc gattggagcg tctgtggcga accctgatgc gattgttgtg    1380
gacattgacg gtgatggaag cttcataatg aacgttcaag agctggccac aatccgtgta    1440
gagaatcttc ctgtgaagat actcttgtta aacaaccagc atcttgggat ggtcatgcaa    1500
tgggaagatc ggttctacaa agctaacaga gctcacactt atctcgggga cccggcaagg    1560
gagaacgaga tcttccctaa catgctgcag tttgcaggag cttgcgggat tccagctgcg    1620
agagtgacga agaaagaaga actccgagaa gctattcaga caatgctgga tacacctgga    1680
```
ccgtacctgt tggatgtcat ctgtccgcac caagaacatg tgttaccgat gatcccaagt    1740
ggtggcactt tcaaagatgt aataaccgaa ggggatggtc gcactaagta ctgagagatg    1800
aagctggtga tcgatcatat ggtaaaagac ttagtttcag ttttcagttt cttttgtgtg    1860
gtaatttggg tttgtcagtt gttgtactgc ttttggtttg ttcccagatt tactcgctgt    1920
tgttgttttg tttccttttt cttttatata                                    1950

<210> SEQ ID NO 9
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
cacaagtctc gtgttataaa ac                                              22

<210> SEQ ID NO 10
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
cattgagtgc caaacatatg aa                                              22

<210> SEQ ID NO 11
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
catacctgtt ggatgtgata t                                               21

<210> SEQ ID NO 12
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
aaacaacaac agcgagtacg t                                               21

<210> SEQ ID NO 13
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
cacaagcctc gtgttataaa aa                                              22

<210> SEQ ID NO 14
<211> LENGTH: 23

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
cattgagtgc caaacattat gta                                              23

<210> SEQ ID NO 15
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
actcggagct atgggtttc                                                   19

<210> SEQ ID NO 16
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
atccaacagg tacggtcca                                                   19

<210> SEQ ID NO 17
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
tgggatggtc atgcaatg                                                    18

<210> SEQ ID NO 18
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
cttgggatgg tcatgcaatt                                                  20

<210> SEQ ID NO 19
<211> LENGTH: 2378
<212> TYPE: DNA
<213> ORGANISM: Brassica napus

<400> SEQUENCE: 19
agattcgttt ctattcatcc ataattaata aaaaaaaag accaaacaaa caaaaatcat        60
attccaaggg tatttcgta aacaaacaaa accctcacaa gtctcgtttt ataaaacgat       120
```

```
tcacgttcac aaactcattc atcatctctc tctcctctaa ccatggcggc ggcaacatcg    180
tcttctccga tctccttaac cgctaaacct tcttccaaat cccctctacc catttccaga    240
ttctcccttc ccttctcctt aaccccacag aaagactcct cccgtctcca ccgtcctctc    300
gccatctccg ccgttctcaa ctcacccgtc aatgtcgcac ctccttcccc tgaaaaaacc    360
gacaagaaca agactttcgt ctcccgctac gctcccgacg agcccgcaa gggtgctgat     420
atcctcgtcg aagccctcga gcgtcaaggc gtcgaaaccg tctttgctta tcccggaggt    480
gcttccatgg agatccacca agccttgact cgctcctcca ccatccgtaa cgtccttccc    540
cgtcacgaac aaggaggagt cttcgccgcc gagggttacg ctcgttcctc cggcaaaccg    600
ggaatctgca tagccacttc gggtcccgga gctaccaacc tcgtcagcgg gttagcagac    660
gcgatgcttg acagtgttcc tcttgtcgcc attacaggac aggtccctcg ccggatgatc    720
ggtactgacg ccttccaaga gacaccaatc gttgaggtaa cgaggtctat tacgaaacat    780
aactatttgg tgatggatgt tgatgacata cctaggatcg ttcaagaagc tttctttcta    840
gctacttccg gtagacccgg accggttttg gttgatgttc ctaaggatat tcagcagcag    900
cttgcgattc ctaactggga tcaacctatg cgcttacctg gctacatgtc taggttgcct    960
cagcctccgg aagtttctca gttaggtcag atcgttaggt tgatctcgga gtctaagagg   1020
cctgttttgt acgttggtgg tggaagcttg aactcgagtg aagaactggg gagatttgtc   1080
gagcttactg ggatccccgt tgcgagtact ttgatggggc ttggctctta tccttgtaac   1140
gatgagttgt ccctgcagat gcttggcatg cacgggactg tgtatgctaa ctacgctgtg   1200
gagcatagtg atttgttgct ggcgtttggt gttaggtttg atgaccgtgt cacgggaaag   1260
ctcgaggctt tcgctagcag ggctaaaatt gtgcacatag acattgattc tgctgagatt   1320
gggaagaata agacacctca cgtgtctgtg tgtggtgatg taaagctggc tttgcaaggg   1380
atgaacaagg ttcttgagaa ccgggcggag gagctcaagc ttgatttcgg tgtttggagg   1440
agtgagttga gcgagcagaa acagaagttc cctttgagct tcaaaacgtt tggagaagcc   1500
attcctccgc agtacgcgat tcagatcctc gacgagctaa ccgaagggaa ggcaattatc   1560
agtactggtg ttggacagca tcagatgtgg gcggcgcagt tttacaagta caggaagccg   1620
agacagtggc tgtcgtcatc aggcctcgga gctatgggtt ttggacttcc tgctgcgatt   1680
ggagcgtctg tggcgaaccc tgatgcgatt gttgtggata ttgacggtga tggaagcttc   1740
ataatgaacg ttcaagagct ggccacaatc cgtgtagaga atcttcctgt gaagatactc   1800
ttgttaaaca accagcatct tgggatggtc atgcaatggg aagatcggtt ctacaaagct   1860
aacagagctc acacttatct cggggacccg gcaagggaga acgagatctt ccctaacatg   1920
ctgcagtttg caggagcttg cgggattcca gctgcgagag tgacgaagaa agaagaactc   1980
cgagaagcta ttcagacaat gctggataca ccaggaccat acctgttgga tgtgatatgt   2040
ccgcaccaag aacatgtgtt accgatgatc ccaagtggtg cactttcaa agatgtaata    2100
acagaagggg atggtcgcac taagtactga gagatgaagc tggtgatcga tcatatggta   2160
aaagacttag tttcagtttc cagtttcttt tgtgtggtaa tttgggtttg tcagttgttg   2220
tactactttt ggttgttccc agacgtactc gctgttgttg ttttgtttcc ttttctttt    2280
atatataaat aaactgcttg ggtttttttt catatgtttg ggactcaatg caaggaatgc   2340
tactagactg cgattatcta ctaatcttgc taggaaat                           2378
```

<210> SEQ ID NO 20
<211> LENGTH: 2359

<212> TYPE: DNA
<213> ORGANISM: Brassica napus

<400> SEQUENCE: 20

| | | | | | |
|---|---|---|---|---|---|
| aaagaaaaga | ccaaacaaac | aaaaatcata | ttccaagggt | attttcgtaa | acaaacaaaa | 60 |
| ccctcacaag | cctcgtttta | taaaaacgat | tcacgttcac | aaactcattc | atcatctctc | 120 |
| tctcatttct | ctctctctct | catctaacca | tggcggcggc | aacatcgtct | tctccgatct | 180 |
| ccttaaccgc | taaaccttct | tccaaatccc | ctctacccat | ttccagattc | tcccttccct | 240 |
| tctccttaac | cccacagaaa | ccctcctccc | gtctccaccg | tccactcgcc | atctccgccg | 300 |
| ttctcaactc | acccgtcaat | gtcgcacctg | aaaaaaccga | caagatcaag | actttcatct | 360 |
| cccgctacgc | tcccgacgag | ccccgcaagg | gtgctgatat | cctcgtggaa | gccctcgagc | 420 |
| gtcaaggcgt | cgaaaccgtc | ttcgcttatc | ccggaggtgc | ctccatggag | atccaccaag | 480 |
| ccttgactcg | ctcctccacc | atccgtaacg | tcctcccccg | tcacgaacaa | ggaggagtct | 540 |
| tcgccgccga | gggttacgct | cgttcctccg | gcaaaccggg | aatctgcata | gccacttcgg | 600 |
| gtcccggagc | taccaacctc | gtcagcgggt | tagccgacgc | gatgcttgac | agtgttcctc | 660 |
| tcgtcgccat | cacaggacag | gtccctcgcc | ggatgatcgg | tactgacgcg | ttccaagaga | 720 |
| cgccaatcgt | tgaggtaacg | aggtctatta | cgaaacataa | ctatctggtg | atggatgttg | 780 |
| atgacatacc | taggatcgtt | caagaagcat | tctttctagc | tacttccggt | agacccggac | 840 |
| cggttttggt | tgatgttcct | aaggatattc | agcagcagct | tgcgattcct | aactgggatc | 900 |
| aacctatgcg | cttgcctggc | tacatgtcta | ggctgcctca | gccaccggaa | gtttctcagt | 960 |
| taggccagat | cgttaggttg | atctcggagt | ctaagaggcc | tgttttgtac | gttggtggtg | 1020 |
| gaagcttgaa | ctcgagtgaa | gaactgggga | gatttgtcga | gcttactggg | atccctgttg | 1080 |
| cgagtacgtt | gatgggcctt | ggctcttatc | cttgtaacga | tgagttgtcc | ctgcagatgc | 1140 |
| ttggcatgca | cgggactgtg | tatgctaact | acgctgtgga | gcatagtgat | ttgttgctgg | 1200 |
| cgtttggtgt | taggtttgat | gaccgtgtca | cgggaaagct | cgaggcgttt | gcgagcaggg | 1260 |
| ctaagattgt | gcacatagac | attgattctg | ctgagattgg | gaagaataag | acacctcacg | 1320 |
| tgtctgtgtg | tggtgatgta | aagctggctt | tgcaagggat | gaacaaggtt | cttgagaacc | 1380 |
| gggcggagga | gctcaagctt | gatttcggtg | tttggaggag | tgagttgagc | gagcagaaac | 1440 |
| agaagttccc | gttgagcttc | aaaacgtttg | gagaagccat | tcctccgcag | tacgcgattc | 1500 |
| aggtcctaga | cgagctaacc | caagggaagg | caattatcag | tactggtgtt | ggacagcatc | 1560 |
| agatgtgggc | ggcgcagttt | tacaagtaca | ggaagccgag | gcagtggctg | tcgtcctcag | 1620 |
| gactcggagc | tatgggtttc | ggacttcctg | ctgcgattgg | agcgtctgtg | gcgaaccctg | 1680 |
| atgcgattgt | tgtggacatt | gacggtgatg | gaagcttcat | aatgaacgtt | caagagctgg | 1740 |
| ccacaatccg | tgtagagaat | cttcctgtga | agatactctt | gttaaacaac | cagcatcttg | 1800 |
| ggatggtcat | gcaatgggaa | gatcggttct | acaaagctaa | cagagctcac | acttatctcg | 1860 |
| ggacccggc | aagggagaac | gagatcttcc | ctaacatgct | gcagtttgca | ggagcttgcg | 1920 |
| ggattccagc | tgcgagagtg | acgaagaaag | aagaactccg | agaagctatt | cagacaatgc | 1980 |
| tggatacacc | tggaccgtac | ctgttggatg | tcatctgtcc | gcaccaagaa | catgtgttac | 2040 |
| cgatgatccc | aagtggtggc | acttcaaag | atgtaataac | cgaaggggat | ggtcgcacta | 2100 |
| agtactgaga | gatgaagctg | gtgatccatc | atatggtaaa | agacttagtt | tcagttttca | 2160 |
| gtttctttg | tgtggtaatt | tgggtttgtc | agttgttgta | ctgcttttgg | tttgttccca | 2220 |

```
gacttactcg ctgttgttgt tttgtttcct ttttctttta tatataaata aactgcttgg    2280
gtttttttac ataatgtttg ggactcaatg caaggaaatg ctactagact gcgattatct    2340
actaatcttg caaggaaat                                                 2359
```

ASSAY FOR IMIDAZOLINONE RESISTANCE MUTATIONS IN *BRASSICA* SPECIES

This application is a divisional of U.S. patent application Ser. No. 10/695,546, filed Oct. 28, 2003, now U.S. Pat. No. 7,595,177, issued on Sep. 29, 2009, which claims priority under 35 U.S.C. §119(e) to U.S. provisional application Ser. No. 60/421,994, filed Oct. 29, 2002; both of which are hereby incorporated herein in their entirety by reference.

This invention relates generally to compositions and methods for identifying *Brassica* plants having increased tolerance to an imidazolinone herbicide.

BACKGROUND OF THE INVENTION

Canola is the seed derived from any of the *Brassica* species *B. napus*, *B. campestris/rapa*, and certain varieties of *B. juncea*. Canola oil is high in monounsaturated fats, moderate in polyunsaturated fats, and low in saturated fats, having the lowest level of saturated fat of any vegetable oil. Thus canola oil is an important dietary option for lowering serum cholesterol in humans. In addition, the protein meal which is the byproduct of canola oil production has a high nutritional content and is used in animal feeds.

Imidazolinone and sulfonylurea herbicides are widely used in modern agriculture due to their effectiveness at very low application rates and relative non-toxicity in animals. Both of these herbicides act by inhibiting acetohydroxyacid synthase (AHAS; EC 4.1.3.18, also known as acetolactate synthase or ALS), the first enzyme in the synthetic pathway of the branched chain amino acids valine, leucine and isoleucine. Several examples of commercially available imidazolinone herbicides are PURSUIT® (imazethapyr), SCEPTER® (imazaquin) and ARSENAL® (imazapyr). Examples of sulfonylurea herbicides are chlorsulfuron, metsulfuron methyl, sulfometuron methyl, chlorimuron ethyl, thifensulfuron methyl, tribenuron methyl, bensulfuron methyl, nicosulfuron, ethametsulfuron methyl, rimsulfuron, triflusulfuron methyl, triasulfuron, primisulfuron methyl, cinosulfuron, amidosulfuron, fluazasulfuron, imazosulfuron, pyrazosulfuron ethyl and halosulfuron.

Due to their high effectiveness and low toxicity, imidazolinone herbicides are favored for application to many crops, including canola, by spraying over the top of a wide area of vegetation. The ability to spray an herbicide over the top of a wide range of vegetation decreases the costs associated with plantation establishment and maintenance and decreases the need for site preparation prior to use of such chemicals. Spraying over the top of a desired tolerant species also results in the ability to achieve maximum yield potential of the desired species due to the absence of competitive species. However, the ability to use such spray-over techniques is dependent upon the presence of imidazolinone resistant species of the desired vegetation in the spray over area. In addition, because residual imidazolinones persist in a sprayed field, a variety of resistant species is advantageous for crop rotation purposes.

Unfortunately, the *Brassica* species which are the source of canola are closely related to a number of broad leaf cruciferous weeds, for example, stinkweed, ball mustard, wormseed mustard, hare's ear mustard, shepherd's purse, common peppergrass, flixweed, and the like. Thus it was necessary to develop *Brassica* cultivars which are tolerant or resistant to the imidazolinone herbicides. Swanson, et al. (1989) *Theor. Appl. Genet.* 78, 525-530 discloses *B. napus* mutants $P_1$ and $P_2$, developed by mutagenesis of microspores of *B. napus* (cv 'Topas'), which demonstrated tolerance to the imidazolinone herbicides PURSUIT® and ASSERT® at levels approaching ten times the field-recommended rates. The homozygous $P_2$ mutant produced an AHAS enzyme which was 500 times more tolerant to PURSUIT® than wild type enzyme, while the AHAS enzyme from the homozygous $P_1$ mutant was only slightly more tolerant than the wild type enzyme. In field trials, the $P_1$, $P_2$, and $P_1 \times P_2$ hybrid withstood ASSERT® applications up to 800 g/ha with no loss of yield. The $P_1$ and $P_2$ mutations were unlinked and semidominant, and $P_1 \times P_2$ crosses tolerated levels of PURSUIT® higher than those tolerated by either homozygous mutant. Imidazolinone-tolerant cultivars of *B. napus* were developed from the $P_1 \times P_2$ mutants and have been sold as CLEARFIELD® canola. See also, Canadian patent application number 2,340,282; Canadian patent number 1,335,412, and European patent number 284419.

Rutledge, et al. (1991) *Mol. Gen. Genet.* 229, 31-40) discloses the nucleic acid sequence of three of the five genes encoding AHAS isoenzymes in *B. napus*, AHAS1, AHAS2, and AHAS3. Rutledge, et al. discusses the mutants of Swanson, et al. and predicts that the two alleles that conferred resistance to imidazolinone herbicides correspond to AHAS1 and AHAS3. Hattori et al. (1995) *Mol. Gen. Genet.* 246, 419-425 disclose a mutant allele of AHAS3 from a mutant *B. napus* cv Topas cell suspension culture line in which a single nucleotide change at codon 557 leading to an amino acid change from tryptophan to leucine confers resistance to sulfonylurea, imidazolinone, and triazolopyrimidine herbicides. Codon 557 of Hattori, et al. corresponds to codon 556 of the AHAS3 sequence disclosed in Rutledge, et al., supra, and to codon 556 of the AHAS3 sequence set forth as GENBANK accession number gi/17775/emb/Z11526/.

A single nucleotide mutation at codon 173 in a *B. napus* ALS gene, corresponding to AHAS2 of Rutledge et al, supra, leads to a change from Pro to Ser (Wiersma et al. (1989) *Mol. Gen. Genet.* 219, 413-420). The mutant *B. napus* AHAS2 gene was transformed into tobacco to produce a chlorsulfuron tolerant phenotype.

U.S. Pat. Nos. 6,114,116 and 6,358,686 disclose nucleic acid sequences from *B. napus* and *B. oleracea* containing polymorphisms, none of which appears to correspond to the polymorphism disclosed in Hattori, et al., supra.

For commercially relevant *Brassica* cultivars, it is necessary to ensure that each lot of herbicide-resistant seed contains all mutations necessary to confer herbicide tolerance. A method is needed to detect mutations in *Brassica* AHAS1 and AHAS3 genes that confer increased imidazolinone tolerance to commercial cultivars.

SUMMARY OF THE INVENTION

The present invention describes the location and identity of a single nucleotide polymorphism at position 1874 of the AHAS1 gene of *B. napus* as set forth in FIG. 1, the polymorphism being designated as the PM1 mutation. The PM1 mutation confers about 15% of the tolerance to imidazolinone herbicides that is present in CLEARFIELD® canola. CLEARFIELD® canola also contains a second single nucleotide polymorphism at position 1712 of the AHAS3 gene of *B. napus* as set forth in FIG. 2, which corresponds to the tryptophan to leucine substitution described in Hattori et al., supra. For the purpose of the present invention, this polymorphism is designated as the PM2 mutation. The PM2 mutation confers about 85% of the tolerance to imidazolinone herbicides exhibited by CLEARFIELD® canola. Both the PM1 and PM2 mutations are required to produce a *Brassica* plant with sufficient herbicide tolerance to be commercially relevant, as in CLEARFIELD® canola.

Accordingly, the present invention provides methods of identifying a plant having increased tolerance to an imidazolinone herbicide by detecting the presence or absence of the B. napus PM1 and PM2 mutations in the plant. One of the advantages of the present invention is that it provides a reliable and quick means to detect plants with commercially relevant imidazolinone tolerance.

In one embodiment, the invention provides a method of assaying a Brassica plant for imidazolinone herbicide tolerance conferred by the PM1 mutation of the B. napus AHAS1 gene. In this method, genomic DNA is isolated from the plant, and the AHAS1 gene is selectively amplified from the genomic DNA using an AHAS1 forward primer and an AHAS1 reverse primer in a first amplification step, thereby producing an AHAS1 reaction mixture. The AHAS1-specific primers are removed from the AHAS1 reaction mixture to produce a purified AHAS1 reaction mixture. The amplified AHAS1 gene is then further amplified in a second amplification step to produce a portion of the AHAS1 gene containing the site of the PM1 mutation, by combining the purified AHAS1 reaction mixture with a PM1 forward primer and a PM1 reverse primer, wherein the PM1 forward primer and the PM1 reverse primer are nested within the AHAS1 forward and reverse primers. The product of the second amplification step is then denatured and allowed to adopt a conformation determined by intramolecular interactions and base stacking, to produce unique single-stranded structures dependent on sequence composition, also referred to as conformers, and the presence or absence of the PM1 mutation is detected on the basis of the mobility of said single stranded structural conformers in a substrate. The detection step of this embodiment is generally known as single strand conformational polymorphism detection.

In another embodiment, the invention provides a method for assaying a Brassica plant for imidazolinone herbicide tolerance conferred by the PM2 mutation of the B. napus AHAS3 gene. In this method, genomic DNA is isolated from the plant, and the AHAS3 gene is selectively amplified from the genomic DNA using an AHAS3 forward primer and an AHAS3 reverse primer in a first amplification step to produce an AHAS3 reaction mixture. The AHAS3 primers are removed from the AHAS3 reaction mixture to produce a purified AHAS3 reaction mixture. The amplified AHAS3 gene is further amplified in a second amplification step by combining a first aliquot of the purified AHAS3 reaction mixture with at least one primer selective for a portion of said AHAS3 gene which comprises a "G" residue at position 1712 of the AHAS3 gene as depicted in SEQ ID NOs:5 and 8, that is, the "wild type" primer is selective for an AHAS3 gene which is inhibited by imidazolinone herbicides. The amplified AHAS3 gene is further amplified in a third amplification step by combining a second aliquot of the purified AHAS3 reaction mixture with a PM2 primer selective for a portion of said AHAS3 gene containing the PM2 mutation. The amplified first and second aliquots are then analyzed for the presence or absence of the PM2 mutation.

In another embodiment of the invention, presence or absence of both the PM1 mutation and the PM2 mutation in a Brassica plant is determined using the above-described methods.

In yet another embodiment, the invention provides oligonucleotide primers for specific amplification of the B. napus AHAS1 gene and the region of the AHAS1 gene corresponding to the PM1 mutation, and for specific amplification of the B. napus AHAS3 gene and the region of the AHAS3 gene corresponding to the PM2 mutation.

In another embodiment, the invention provides isolated nucleic acids produced as reaction products of the specific amplification of the B. napus AHAS1 gene and the region of the AHAS1 gene corresponding to the PM1 mutation, and isolated nucleic acids produced as reaction products of specific amplification of the B. napus AHAS3 gene and the region of the AHAS3 gene corresponding to the PM2 mutation.

In another embodiment, the invention provides a method of marker-assisted breeding of canola plants using the PM1 and PM2 assays, oligonucleotide primers, and amplification reaction products disclosed herein.

BRIEF DESCRIPTION OF THE DRAWINGS

FIG. 1 shows the aligned nucleic acid sequences of AHAS1 isolated from several varieties of B. napus (SEQ ID NOs: 1-4). The position of the PM1 mutation is indicated (position 1874), as are the positions of preferred PCR amplification primers.

FIG. 2 shows the aligned nucleic acid sequences of AHAS3 from several varieties of B. napus (SEQ ID NOs: 5-8). The position of the PM2 mutation is indicated (position 1712), as are the positions of preferred PCR amplification primers.

FIG. 5 shows the aligned AHAS1 (SEQ ID NO:19) and AHAS3 (SEQ ID NO:20) genes and the positions of the AHAS1 forward amplification primer (SEQ ID NO:9); the AHAS1 reverse amplification primer (SEQ ID NO:10); the AHAS3 forward amplification primer (SEQ ID NO:13); and the AHAS3 reverse amplification primer (SEQ ID NO:14).

DETAILED DESCRIPTION OF THE INVENTION

Figure 3:
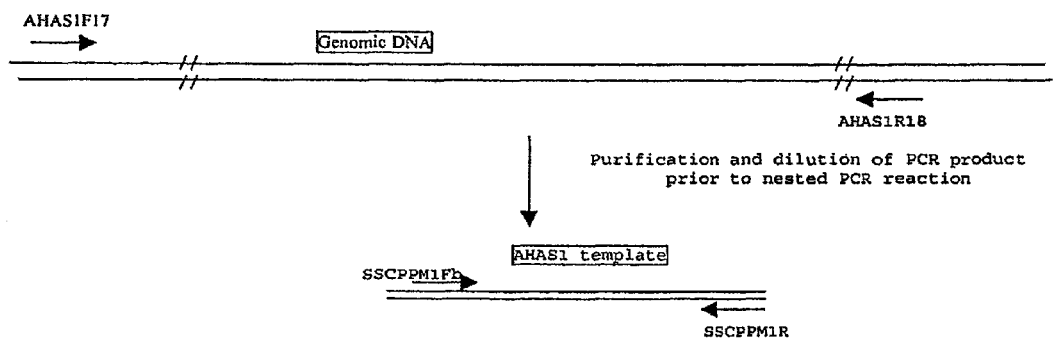
FIG. 3 is a diagram of one embodiment of the present invention's method for detection of the PM1 mutation.
Figure 4:
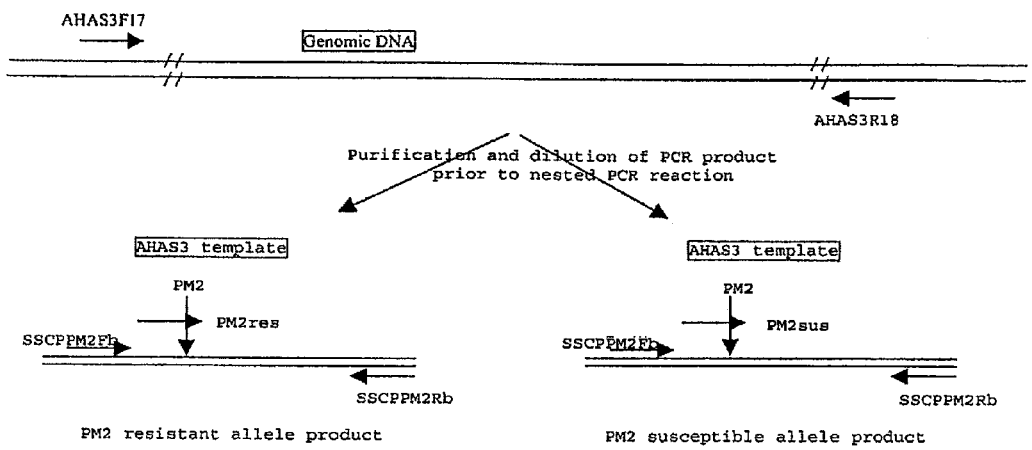
FIG. 4 is a diagram of one embodiment of the present invention's method for detection of the PM2 mutation.

The present invention provides methods and compositions for identifying plants having increased tolerance to an imidazolinone herbicide by virtue of the presence of the B. napus PM1 and PM2 mutations. More particularly, the methods and compositions of the present invention allow identification of Brassica seeds and plants having commercially relevant imidazolinone tolerance, such as CLEARFIELD® canola. In some embodiments, the methods of the invention employ novel polynucleotide primers including PM1 extension primers and PM2 extension primers.

It is to be understood that as used in the specification and in the claims, "a" or "an" can mean one or more, depending upon the context in which it is used. Thus, for example, reference to "a cell" can mean that at least one cell can be utilized.

For the purposes of the present invention, the level of tolerance to imidazolinone herbicides exhibited by CLEARFIELD® canola which contains both the PM1 and PM2 mutations is defined as "100% tolerance", or "commercially relevant imidazolinone tolerance" or "commercial field tolerance". The terms "tolerance" and "resistance" are used interchangeably herein.

An oligonucleotide as defined herein is a nucleic acid comprising from about 8 to about 25 covalently linked nucleotides. A polynucleotide as defined herein is a nucleic acid comprising more than 25 covalently linked nucleotides. In accordance with the invention, oligonucleotides and polynucleotides may comprise nucleic acid analogs, including, without limitation, phosphorothioates, phosphoramidates, peptide nucleic acids, and the like. An "isolated" nucleic acid is substantially of essentially free from components which normally accompany it as found in its native state.

As defined herein, a "PM1 mutation" refers to a single nucleotide polymorphism in a *B. napus* AHAS1 gene in which there is a "G" to "A" nucleotide substitution at position 1874 of the AHAS1 wild type polynucleotide sequence shown in FIG. 1, the mutation being represented in SEQ ID NOs:1 and 3, which substitution leads to a serine to asparagine amino acid substitution at position 638 in the *B. napus* AHAS1 enzyme.

As defined herein, a "PM2 mutation" refers to a single nucleotide polymorphism in a *B. napus* AHAS3 gene in which there is a "G" to "T" nucleotide substitution at position 1712 of the AHAS3 wild type polynucleotide sequence shown in FIG. 2, the mutation being represented in SEQ ID NOs:6 and 7, which substitution leads to a tryptophan to leucine amino acid substitution at position 556 in the *B. napus* AHAS3 enzyme.

The presence of the PM1 and PM2 mutations in a plant confers tolerance to such imidazolinone herbicides as PURSUIT® (imazethapyr, 2-[4,5-dihydro-4-methyl-4-(1-methylethyl)-5-oxo-1H-imidazol-2-yl]-5-ethyl-3-pyridinecarboxylic acid), CADRE® (imazapic, 2-[4,5-dihydro-4-methyl-4-(1-methylethyl)-5-oxo-1H-imidazol-2-yl]-5-methyl-3-pyridinecarboxylic acid), RAPTOR® (imazamox, 2-[4,5-dihydro-4-methyl-4-(1-methylethyl)-5-oxo-1H-imidazol-2-yl]-5-(methoxymethyl)-3-pyridinecarboxylic acid), SCEPTER® (imazaquin, 2-(4,5-dihydro-4-methyl-4-(1-methylethyl)-5-oxo-1H-imidazol-2-yl)-3-quinolinecarboxylic acid), ASSERT® (imazethabenz, methyl esters of 2-[4,5-dihydro-4-methyl-4-(1-methylethyl)-5-oxo-1H-imidazol-2-yl]-4-methylbenzoic acid and 2-[4,5-dihydro-4-methyl-4-(1-methylethyl)-5-oxo-1H-imidazol-2-yl]-5-methylbenzoic acid), ARSENAL® (imazapyr, 2-[4,5-dihydro-4-methyl-4-(methylethyl)-5-oxo-1H-imidazol-2-yl]-3-pyridinecarboxylic acid), and the like. In addition, the PM1 and PM2 mutations may confer resistance to sulfonylurea, triazolopyrimidine, pyrimidinyl(thio)benzoate, and sulfonylamino-carbonyl-triazolinone herbicides.

The PM1 and PM2 mutations may be present in a plant by virtue of mutagenesis of any species of plant containing the *B. napus* AHAS1 and AHAS3 genes, respectively. Alternatively, the PM1 and PM2 mutations may be present in a plant by virtue of transformation of the *B. napus* AHAS1 PM1 gene and the *B. napus* AHAS3 PM2 genes into the plant, using known methods such as those set forth in U.S. Pat. Nos. 5,591,616; 5,767,368; 5,736,369; 6,020,539; 6,153,813; 5,036,006; 5,120,657; 5,969,213; 6,288,312; 6,258,999, and the like. Preferably, the plant is a *Brassica* oilseed. More preferably, the plant species is selected from the group consisting of *B. napus*, *B. campestris/rapa*, and *B. juncea*. Most preferably, the plant species is *B. napus*. In accordance with the present invention, the term "plant" includes seeds, leaves, stems, whole plants, organelles, cells, and tissues.

In the first step of the methods of the invention, genomic DNA is isolated from the plant. It is to be understood that when practicing the methods of the present invention, genomic DNA can be extracted from the plant by any method known to those of skill in the art. Genomic DNA can be extracted from a whole plant, a plant leaf, a plant stem, a plant seed, or any plant organelle, cell or tissue. One non-limiting method for extracting the DNA from a plant leaf is described in Example 1 below.

When assaying for the presence or absence of the PM1 mutation, in the second step the AHAS1 gene is selectively amplified from the isolated genomic DNA. Amplification can be achieved using any method known to those of skill in the art including PCR. The term "PCR" as used herein refers to the polymerase chain reaction method of DNA amplification. As will be understood by one of ordinary skill in the art, this term also includes any and all other methods known in the art for nucleic acid amplification requiring an amplification target, at least one primer and a polymerase. For example, the AHAS1 gene, or a portion thereof which contains the site of the PM 1 mutation, may be amplified by combining the isolated genomic DNA with an appropriate primer set for the amplification of a polynucleotide sequence containing a PM1 mutation. Each primer set consists of a forward primer and a reverse primer, each of which can be referred to as an "amplification primer." In one embodiment of the present invention, the AHAS1 gene may be amplified using a primer set wherein the AHAS1 forward amplification primer comprises the sequence 5' CACAAGTCTCGTGTTATAAAAC 3' (SEQ ID NO:9) and the AHAS1 reverse amplification primer comprises the sequence 5' CATTGAGTGCCAAACATATGAA 3' (SEQ ID NO:10). Those of skill in the art will recognize that other primers may be used to selectively amplify the *B. napus* AHAS1 gene. As is well known, amplification occurs through cycles of incubation of the genomic DNA, the primers, a thermostable DNA polymerase, and nucleotides under conditions suitable for DNA synthesis, as described in U.S. Pat. Nos. 4,683,195; 4,683,202; 4,965,188; 5,998,143, and the like. Apparatus and reagents suitable for PCR amplification are commercially available, for example, from Applied Biosystems, Inc. Foster City, Calif.

After the first amplification step, the AHAS1 amplification reaction product or mixture is purified to remove the AHAS1-specific amplification primers. Any method may be used for this purification step. Preferably, commercially available PCR purification methods such as the Wizard MagneSil PCR Cleanup System (ProMega, Madison, Wis., USA) is used to remove the AHAS1 amplification primers from the AHAS1 amplification mixture. More preferably, the AHAS1 amplification primers are removed by exonuclease digestion. Any exonuclease capable of specifically digesting single stranded DNA may be used for the digestion. For example, Exonuclease T (RNAase T), S1 nuclease from *Aspergillus oryzae*, Mung bean nuclease, or Exonuclease I from *Escherichia coli* may be used to remove the AHAS1 amplification primers. Preferably, Exonuclease I use used to remove the AHAS1 amplification primers.

In the third step of the PM1 assay of the invention, the portion of the amplified AHAS1 gene that contains the site of the PM1 mutation, that is, position 1874 of SEQ ID NOs:1-4, is further amplified in a second amplification step, using a PM1 forward primer and a PM1 reverse primer. The PM1 forward primer and the PM1 reverse primer are complementary to a portion of the AHAS1 gene within the portion amplified by the AHAS1 forward primer and the AHAS1 reverse primer, as depicted in FIG. 1, and are thus "nested" within the primers that amplify the AHAS1 gene. In a preferred embodiment, the PM1 forward primer comprises the sequence 5' CATACCTGTTGGATGTGATAT 3' (SEQ ID NO:11), and the PM1 reverse primer comprises the sequence 5' AAACAACAACAGCGAGTACGT 3' (SEQ ID NO:12). Those of skill in the art will recognize that other primers may be used to selectively amplify the portion of the *B. napus* AHAS1 gene which corresponds to the PM1 mutation. In accordance with the invention, the portion of the amplified AHAS1 gene that contains the site of the PM1 mutation may optionally be labeled using a radioactive tracer, a fluorescent dye, a luminescent label, a paramagnetic label, or any other label suitable for detection of nucleic acids.

In the fourth step of the PM1 assay of the invention, the product of the second amplification step is denatured and placed under conditions that lead to the adoption of a specific single-stranded conformation, dependent on its nucleotide sequence. A variety of methods for denaturing and partial reannealing nucleic acids is known in the art, and any such method may be used in this step of the PM1 assay of the invention. Preferably, the polynucleotides are denatured using heat treatment, for example, exposure to temperatures of 90° C. or greater for about ten minutes, and partially renatured by rapid cooling on ice. Alternatively, the polynucleotides containing the site of the PM1 mutation may be denatured using treatment with alkali and partially renatured by addition of acid to reduce the pH.

In the final step of the PM1 assay of the invention, the presence or absence of the PM1 mutation is detected on the basis of the mobility of the polynucleotide conformer in a substrate. Any detection method suitable for separating polynucleotides may be used in this step, for example, gel electrophoresis, high performance liquid chromatography, capillary electrophoresis, and the like. Substrates for such methods are well known, and include, without limitation, polyacrylamide, linear polyacrylamide, poly(N,N-dimethylacrylamide), hydroxyalkyl cellulose, polyoxyethylene, F127 (copolymer of polyoxyethylene and polyoxypropylene, BASF, Ludwigshafen, Germany), agarose, diethylaminoethyl cellulose, sepharose, GENESCAN (Applied Biosystems, Foster City, Calif., USA), POP (Amersham Biosciences AB, Uppsala, SE), and the like. When the amplified nucleic acid has been labeled, the detection step may include detection of the radioactive, fluorescent, luminescent, paramagnetic, or other label. When the amplified nucleic acid has not been labeled, detection of the single stranded polynucleotide conformers in the substrate may be performed using known methods, such as silver staining, fluorescent and the like.

In accordance with the invention, the presence of the PM2 mutation may be inferred from resistance to an imidazolinone herbicide applied to the plant or assay of AHAS activity in the presence of an imidazolinone herbicide. Plants may then be assayed using the PM1 assay set forth above to determine whether the plant exhibits commercially relevant imidazolinone tolerance.

Alternatively, the plant may be assayed for the presence of the PM2 mutation using the PM2 assay method of the invention, in which the AHAS3 gene is selectively amplified from isolated genomic DNA in a first amplification step. For this step, an AHAS3 forward primer and an AHAS3 reverse primer is combined with the genomic DNA and subjected to PCR amplification as described above. A preferred AHAS3 forward primer for use in this method of the invention comprises the sequence 5' CACAAGCCTCGTGTTATAAAAA 3' (SEQ ID NO:13), and a preferred AHAS3 reverse primer comprises the sequence 5' CATTGAGTGCCAAACATTATGTA 3' (SEQ ID NO:14). Those of skill in the art will recognize that other primers may be used to selectively amplify the *B. napus* AHAS3 gene.

After the first amplification step, the AHAS3 amplification reaction product or mixture is purified to remove the AHAS3-specific amplification primers. Any of the purification methods described above may be used for this step. Preferably, Exonuclease I is used to remove the AHAS3 amplification primers.

After the purification step, the amplified AHAS3-containing DNA is divided into at least two aliquots, each of which is separately amplified in the region of the AHAS3 gene surrounding position 1712 of SEQ ID NOs:5-8, hereinafter referred to as the "PM2 region". A first aliquot of the amplified AHAS3 DNA is further amplified in a second amplification step, using at least one primer which is selective for a portion of the AHAS3 gene that is wild type at position 1712 of said gene, that is, which comprises a "G" residue at said position 1712, as depicted in SEQ ID NOs:5 and 8. In a preferred embodiment, the second amplification step employs a wild type-selective forward primer in combination with a forward and reverse primers that selectively amplify the PM2 region. All three of these primers are nested within the primers employed to amplify the AHAS3 gene in the first amplification step. In a preferred embodiment, the forward primer for amplification of the PM2 region comprises the sequence 5' ACTCGGAGCTATGGGTTTC 3' (SEQ ID NO:15), and the reverse primer for amplification of the PM2 region comprises the sequence 5' ATCCAACAGGTACGGTCCA 3' (SEQ ID NO:16), the wild type selective primer comprises the sequence 5' TGGGATGGTCATGCAATG 3' (SEQ ID NO:17). Those of skill will recognize that other primers may be used to amplify the PM2 region.

In accordance with the invention, a second aliquot of the amplified and purified AHAS3-containing DNA is further amplified in a third amplification step, using at least one primer which is selective for the PM2 mutation, that is, which comprises a "T" residue at said position 1712 of the AHAS3 gene, as depicted in SEQ ID NOs:6 and 7. In a preferred embodiment, the second amplification step employs a PM2-selective forward primer in combination with a forward and reverse primers that selectively amplify the PM2 region. All three of these primers are nested within the primers employed to amplify the AHAS3 gene in the first amplification step. In a preferred embodiment, the PM2-selective primer comprises the sequence 5' CTTGGGATGGTCATGCAATT 3' (SEQ ID NO:18), the forward primer for amplification of the PM2 region comprises the sequence 5' ACTCGGAGCTATGGGTTTC 3' (SEQ ID NO:15), and the reverse primer for amplification of the PM2 region comprises the sequence 5' ATCCAACAGGTACGGTCCA 3' (SEQ ID NO:16). Those of skill will recognize that other primers may be used to amplify the PM2 region.

The second and third amplification steps may be performed iteratively or simultaneously.

In accordance with the invention, in the second and third amplification steps, the portion of the amplified AHAS3 gene that contains the site of the PM2 mutation may optionally be labeled using a radioactive tracer, a fluorescent dye, a luminescent label, a paramagnetic label, or any other label suitable for detection of nucleic acids.

In the final step of the PM2 assay of the invention, the products of the second and third amplification steps are analyzed for the presence or absence of the PM2 mutation using known methods, such as gel electrophoresis, high performance liquid chromatography, capillary electrophoresis, and the like. When the amplified nucleic acids have been labeled, the analysis step may include detection of the radioactive, fluorescent, luminescent, paramagnetic, or other label. When the amplified nucleic acids have not been labeled, the analysis step may be performed using known methods, such as ethidium bromide staining, and the like.

The invention is also embodied in isolated nucleic acids which are formed as reaction products of the amplifications described herein. In one embodiment, the nucleic acid reaction product corresponds to the region of the AHAS1 gene between the AHAS1 forward amplification primer and the AHAS1 reverse amplification primer, and has a sequence as set forth from nucleotide 96 to nucleotide 2330 of SEQ ID NO:19. In another embodiment, the nucleic acid reaction product corresponds to the region of the AHAS1 gene between the PM1 forward primer and the PM1 reverse primer and is exemplified by a sequence as set forth from nucleotide 1817 to nucleotide 2063 of SEQ ID NO:1; a sequence as set forth from nucleotide 1735 to nucleotide 1980 of SEQ ID NO:2; a sequence as set forth from nucleotide 1809 to nucleotide 2054 of SEQ ID NO:3; and a sequence as set forth from nucleotide 1720 to nucleotide 1966 of SEQ ID NO:4.

In another embodiment, the nucleic acid reaction product corresponds to the region of the AHAS3 gene between the AHAS3 forward amplification primer and the AHAS3 reverse amplification primer, and has a sequence as set forth from nucleotide 64 to nucleotide 2310 of SEQ ID NO:20. The invention is further embodied by a nucleic acid corresponding to the PM2 region of the AHAS3 gene, between the PM2 forward primer and the PM2 reverse primer. Examples of these reaction products include nucleic acids having a sequence as set forth from nucleotide 1383 to nucleotide 1770 of SEQ ID NO:5; nucleic acids having a sequence as set forth from nucleotide 1518 to nucleotide 1905 of SEQ ID NO:6; nucleic acids having a sequence as set forth from nucleotide 1352 to nucleotide 1739 of SEQ ID NO:7; and nucleic acids having a sequence as set forth from nucleotide 1308 to nucleotide 1695 of SEQ ID NO:8. Additional nucleic acids are encompassed in this embodiment as the reaction products of the third amplification reaction of the PM2 assay, that is, nucleic acids having a sequence as set forth from nucleotide 1560 to nucleotide 1770 of SEQ ID NO:5; nucleic acids having a sequence as set forth from nucleotide 1695 to nucleotide 1905 of SEQ ID NO:6; nucleic acids having a sequence as set forth from nucleotide 1529 to nucleotide 1739 of SEQ ID NO:7; and nucleic acids having a sequence as set forth from nucleotide 1485 to nucleotide 1695 of SEQ ID NO:8.

The PM1 and PM2 assays, oligonucleotides, and nucleic acid reaction products may also be used in a marker assisted breeding program to make progeny canola plants by selective breeding. In such a program, other markers in addition to the PM1 and PM2 polymorphisms would be required, as is known in the art. Methods of marker assisted selection are described, for example, in U.S. Pat. No. 6,100,030.

The invention is further illustrated by the following examples, which are not to be construed in any way as imposing limitations upon the scope thereof.

Example 1

Materials and Genomic DNA Isolation

The canola lines used for these experiments are listed in Table 1 below. The nucleic acid sequences of the AHAS1 genes from each of these lines are shown in FIG. 1, and the nucleic acid sequences of the AHAS3 genes for each of these lines are shown in FIG. 2.

TABLE 1

| Lines | Mutations | Code | Herbicide resistance |
|---|---|---|---|
| T9107 | Point mutation 1 on AHAS1 | PM 1 | Partial resistant |
| T9I08 | Point mutation 2 on AHAS3 | PM2 | Partial resistant |
| TR101 | Point mutation 1 + 2 | R | Resistant |
| OPTION 501 | wild type | S | Susceptible |

Plants were grown from seeds of each canola line. Three to five leaf punches from each plant were combined in each sample, and samples were freeze dried. The freeze dried samples were ground by adding cleaned BB's (BB's were washed with soap and water and then dried with organic solvent prior to use) to each sample and shaking the samples until a fine powder was obtained (approximately one minute). Five hundred µl of Extraction Buffer (1300 µl 1M Tris; 4.15 ml dd $H_2O$; 325 µl 0.5M EDTA; 650 µl 10% SDS) was added to each sample, and the samples were inverted several times. The samples were then placed into a 65° C. water bath for 60 minutes, with inversions every 20 minutes. During the sample incubation, a second set of test tubes was filled with 400 µl isopropanol.

After the incubation period, the samples were allowed to cool for 5 minutes and centrifuged briefly in a microfuge. Five µl RNAase A (10 mg/ml) was added to each sample tube, and the tubes were inverted about 20 times. The samples were again centrifuged briefly in a microfuge and allowed to sit at room temperature for 30 minutes. To each sample was added 170 µl 7.5M ammonium acetate, and samples were shaken for approximately 2 minutes to precipitate protein. The samples were then centrifuged briefly in a microfuge, placed on ice for 15 minutes, and then re-centrifuged for 15 minutes. The supernatants were retained and placed into the previously prepared isopropanol-containing test tubes, which were then gently inverted approximately 50 times to precipitate DNA. The sample tubes were then centrifuged at maximum rpm for 15 minutes. The supernatants from this centrifugation were discarded, and the DNA pellets were washed once with 300 µl 95% ethanol and twice with 300 µl 70% ethanol. After being allowed to dry overnight, the washed DNA pellets were resuspended in 50 µl ddH20 for further analysis.

Example 2

PM1 Assay

A single strand conformational polymorphism (SSCP) analysis was carried out by denaturing products of two rounds of PCR which selectively amplified the region of the *Brassica* AHAS1 gene that corresponds to the PM1 mutation, that is, the region surrounding position 1874 of SEQ ID NOs:1-4, and allowing each of the single strands to reanneal partially with itself. The conformation of each of the single strands, along with its nucleotide sequence, determines its mobility in a non-denaturing gel.

A. AHAS1-Specific Amplification Step

The conditions used for the first round of PCR amplification are listed in Table 2. The AHAS1-specific forward primer used for the first amplification step had the sequence 5' CACAAGTCTCGTGTTATAAAAC 3' (SEQ ID NO:9) and the AHAS1-specific reverse primer used had the sequence 5' CATTGAGTGCCAAACATATGAA 3' (SEQ ID NO:10). A Tetrad thermocycler (MJ Research) was used for PCR amplification. The first round PCR reactions consisted of an initial denature of 5 minutes at 94° C. followed by 25 cycles (30 seconds at 94° C., 1 minute at 60° C., 1 minute at 72° C.), with a final extension of 10 minutes at 72° C. To 2 µl of the product of the first round of amplification, 0.5 unit ExoI (Exonuclease I) was added and incubated at 37° C. for 1 hour before the enzyme was inactivated at 72° C. for 15 minutes. 100 µL of deionized distilled water (dd$H_2O$) was added following the ExoI reaction.

TABLE 2

|  | Final concentration |
|---|---|
| Genomic DNA | ±10 ng |
| Buffer (BRL - 10 x) | 1 x |
| MgCl$_2$ (BRL - 50 mM) | 2.5 mM |
| dNTPs | 0.2 mM |
| Primer forward | 0.5 µM |
| Primer reverse | 0.5 µM |
| Taq (BRL - 5 U/µl) | 0.4 U |
| H$_2$O | → 15 µl |

B. PM1-Specific Amplification Step

The conditions used for the second round of the PCR amplification are shown in Table 3. The reaction consisted of an initial denature of 5 min at 94° C. followed by 35 cycles (30 seconds at 94° C., 1 minute at 65° C., 1 minute at 72° C.), with a final extension of 10 minutes at 72° C. The PM1-specific primers are nested within the primers used to amplify the AHAS1 gene and thus specifically amplify the region surrounding position 1874 of SEQ ID NOs:1-4. The PM1-specific forward primer used in the second amplification step had the sequence 5' CATACCTGTTGGATGTGATAT 3' (SEQ ID NO: 11), and the PM1-specific reverse primer had the sequence 5' AAACAACAACAGCGAGTACGT 3' (SEQ ID NO:12).

TABLE 3

|  | Final concentration |
|---|---|
| Diluted AHAS1 PCR product | 1 µl |
| Buffer (BRL - 10 x) | 1 x |
| MgCl$_2$ (BRL - 50 mM) | 2 mM |
| dNTPs | 0.2 mM |
| Primer forward | 0.5 µM |
| Primer reverse | 0.5 µM |
| Taq (BRL - 5 U/µl) | 0.4 U |
| H$_2$O | → 15 µl |

C. SSCP Analysis of PIM1 Amplification Products

An 8 M urea stop solution containing bromo phenol blue, xylene cyanol and Orange G tracking dyes was added to a final concentration of 5M. The mixtures were denatured for 10 minutes at 90° C. and quickly cooled on ice. The SSCPs were electrophoresed on a 12% non-denaturing acrylamide/bisacrylamide (49:1) in 0.5×Tris borate EDTA (TBE) buffer. The gels were run at constant amperage of 17 mA for 20-24 hours at 4° C. The DNA was visualized by silver staining. The resulting gel clearly and accurately identified the presence or absence of imidazolinone resistant (PM1) and susceptible (wild type) alleles for all tested strains.

Example 3

PM2 Assay

This assay employed a first round of PCR which selectively amplifies the AHAS3 gene, after which the amplification product was divided into two aliquots. Each aliquot was then amplified separately, using sets of three primers nested within those used for amplifying the AHAS3 gene. The three primers selectively amplify the region of the AHAS3 gene corresponding to the PM2 mutation, that is, the region surrounding position 1712 of SEQ ID NOs; 5-8. Separate PCR steps were performed on each aliquot, one which selectively amplifies nucleic acids containing the PM2 mutation and one which selectively amplifies wild type nucleic acids. The presence of wild type or PM2 was detected by gel electrophoresis.

A. AHAS3-Specific Amplification Step

The conditions used for the first round of amplification are shown in Table 4. The AHAS3-specific forward primer used for the first amplification step had the sequence 5' CACAAGCCTCGTGTTATAAAAA 3' (SEQ ID NO:13), and the AHAS3-specific reverse primer had the sequence 5' CATTGAGTGCCAAACATTATGTA 3' (SEQ ID NO:14). The PCR reactions consisted of an initial denature of 5 minutes at 94° C. followed by 25 cycles (30 seconds at 94° C., 1 minute at 60° C., 1 second at 72° C.), with a final extension of 10 minutes at 72° C. To 2 µl of this PCR product, 0.5 unit ExoI was added and incubated at 37° C. for 1 hour before the enzyme was inactivated at 72° C. for 15 minutes. 100 µL of ddH$_2$O was added following the ExoI reaction.

TABLE 4

|  | Final concentration |
|---|---|
| Genomic DNA | ±10 ng |
| Buffer (BRL - 10 x) | 1 x |
| MgCl$_2$ (BRL - 50 mM) | 2.5 mM |
| dNTPs | 0.2 mM |
| Primer forward | 0.5 µM |
| Primer reverse | 0.5 µM |
| Taq (BRL - 5 U/µl) | 0.4 U |
| H$_2$O | → 15 µl |

B. PM2 Region-Specific Amplification Steps

The conditions used for the second round of the nested PCR with the different primer sets are described in Table 5. The PM2 region-specific primers are nested within the primers used to amplify the AHAS3 gene and thus specifically amplify the region surrounding position 1712 of SEQ ID NOs:5-8. The PM2 region-specific forward primer (PM2 F in Table 5) had the sequence 5' ACTCGGAGCTATGGGTTTC 3' (SEQ ID NO:15), and the PM2 region-specific reverse primer (PM2 R in Table 5) had the sequence 5' ATCCAACAGGTACGGTCCA 3' (SEQ ID NO:16). The amplification primer specific for the wild type allele at position 1712 (PM2 sus in Table 5) had the sequence 5' TGGGATGGTCATGCAATG 3' (SEQ ID NO:17), and the primer specific for the PM2 mutation (PM2 res in Table 5) had the sequence 5' CTTGGGATGGTCATGCAATT 3' (SEQ ID NO:18). The cycling conditions for the second and third amplification steps were as follows: an initial denature of 5 min at 94° C. followed by 38 cycles (30 at seconds 94° C., 45 seconds at 65° C., 60 seconds at 72° C.), with a final extension of 10 minutes at 72° C.

TABLE 5

|  | Wild type | PM2 |
|---|---|---|
| Diluted AHAS3 PCR product | 1 µl | 1 µl |
| Buffer (BRL - 10 x) | 1 x | 1 x |
| MgCl$_2$ (BRL - 50 mM) | 2 mM | 2 mM |
| dNTPs | 0.2 mM | 0.2 mM |
| PM2 F | 0.5 µM | 0.5 µM |
| PM2 res |  | 0.5 µM |
| PM2 sus | 0.5 µM |  |
| PM2 R | 0.5 µM | 0.5 µM |
| Taq (BRL - 5 U/µl) | 0.4 U | 0.4 U |
| H$_2$O | → 15 µl | → 15 µl |

After amplification was complete, 6× loading buffer was added to all reactions, (4 g sucrose, 2.4 mL 0.5M EDTA, bromophenol blue, xylene cyanol and Orange G to final 10 mL volume). The products of the second and third amplification steps were run on a 3.5% metaphor gel for 4 hours at 92 V. Each amplification reaction yielded two PCR fragments: a larger PCR fragment resulting from the PM2 region specific primers and a smaller PCR fragment created by amplification of the wild type-specific primer or PM2-specific primer in combination with the reverse PM2 region specific primer. The larger fragment was used as a positive control for the PCR reaction. The smaller PCR fragment was an allele-specific PCR product. The gel clearly and accurately identified the presence or absence of imidazolinone resistant (PM2) and susceptible (wild type) alleles for all tested strains.

That which is claimed:

1. A first primer set comprising a first synthetic oligonucleotide consisting of SEQ ID NO: 18, a second synthetic oligonucleotide comprising SEQ ID NO: 16, and a third synthetic oligonucleotide comprising SEQ ID NO: 15, wherein the first primer set is capable of specifically amplifying by PCR a region of the *B. napus* AHAS 3 gene comprising the PM2 mutation.

2. The primer set according to claim 1, further comprising a second primer set capable of specifically amplifying the AHAS3 gene.

3. The primer set of claim 2, wherein the second primer set comprises a synthetic oligonucleotide comprising SEQ ID NO: 13, and a synthetic oligonucleotide comprising SEQ ID NO: 14.

* * * * *

UNITED STATES PATENT AND TRADEMARK OFFICE
CERTIFICATE OF CORRECTION

| | | |
|---|---|---|
| PATENT NO. | : 8,829,169 B2 | Page 1 of 1 |
| APPLICATION NO. | : 12/545147 | |
| DATED | : September 9, 2014 | |
| INVENTOR(S) | : Barnes et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 32 days.

Signed and Sealed this
Twenty-fifth Day of August, 2015

Michelle K. Lee
*Director of the United States Patent and Trademark Office*